(12) United States Patent
Taguchi et al.

(10) Patent No.: US 8,563,281 B2
(45) Date of Patent: Oct. 22, 2013

(54) METHOD FOR PRODUCTION OF POLYESTER COPOLYMER USING RECOMBINANT MICROORGANISM

(75) Inventors: Seiichi Taguchi, Sapporo (JP); Kenji Tajima, Sapporo (JP); Yasuharu Satoh, Sapporo (JP); Ken'ichiro Matsumoto, Sapporo (JP); Miwa Yamada, Sapporo (JP); Shusei Obata, Nagoya (JP); Hiromi Kambe, Seto (JP); Katsunori Kohda, Aichi-gun (JP); Katsuhiro Ohno, Aichi-gun (JP); Takashi Shimamura, Aichi-gun (JP)

(73) Assignee: Toyota Jidosha Kabushiki Kaisha, Aichi (JP)

( * ) Notice: Subject to any disclaimer, the term of this patent is extended or adjusted under 35 U.S.C. 154(b) by 109 days.

(21) Appl. No.: 12/989,333

(22) PCT Filed: Apr. 23, 2009

(86) PCT No.: PCT/JP2009/058092
§ 371 (c)(1),
(2), (4) Date: Jan. 7, 2011

(87) PCT Pub. No.: WO2009/131186
PCT Pub. Date: Oct. 29, 2009

(65) Prior Publication Data
US 2011/0104768 A1    May 5, 2011

(30) Foreign Application Priority Data

Apr. 23, 2008   (JP) .................................. 2008-113127
Oct. 27, 2008   (JP) .................................. 2008-298765

(51) Int. Cl.
*C12P 7/62*     (2006.01)
*C12N 1/20*     (2006.01)
*C12N 1/00*     (2006.01)

(52) U.S. Cl.
USPC .................... 435/135; 435/252.3; 435/252.33; 435/254.11

(58) Field of Classification Search
None
See application file for complete search history.

(56) References Cited

U.S. PATENT DOCUMENTS

| 5,266,470 | A | 11/1993 | Senior et al. |
| 5,292,860 | A | 3/1994 | Shiotani et al. |
| 5,643,758 | A | 7/1997 | Guan et al. |
| 5,981,257 | A | 11/1999 | Fukui et al. |
| 2004/0076982 | A1 | 4/2004 | Gokarn et al. |
| 2007/0054386 | A1 | 3/2007 | Taguchi et al. |

FOREIGN PATENT DOCUMENTS

| EP | 2284261 | A1 | 2/2011 |
| JP | 57-150393 | A | 9/1982 |
| JP | 61-293385 | A | 12/1986 |
| JP | 5-74492 | A | 3/1993 |
| JP | 5-39049 | A | 4/1993 |
| JP | 5-93049 | A | 4/1993 |
| JP | 7-79705 | B2 | 8/1995 |
| JP | 07-265065 | A | 10/1995 |
| JP | 10-108682 | A | 4/1998 |
| JP | 2004-514431 | T | 5/2004 |
| WO | 02/42418 | A2 | 5/2002 |
| WO | 03/100055 | A1 | 12/2003 |
| WO | 2006/126796 | A1 | 11/2006 |
| WO | 2008/062996 | A1 | 5/2008 |
| WO | 2008/062999 | A1 | 5/2008 |
| WO | 2009/031762 | A2 | 3/2009 |

OTHER PUBLICATIONS

Babel, T et al. Construction of *Escherichia coli* K-12 in-frame single-gene knockout mutants: the Keio collection. Molecular Systems Biology. 2006. p. 1-11.*
Coli Genetic Stock Center. Yale University. 2006. p. 1-6.*
Pohlmann, A et al. Acety-CoA acetyltransferase (*Ralstonia eutropha*). GenBank YP_725941.1. 2006 p. 1-2.*
Pohlmann, A et al. acetoacetyl-CoA reductase (*Ralstonia eutropha*). GenBank YP_726636.1. 2006. p. 1-2.*
Selmer, T et al. propionate CoA-transferase (*Clostridium propionicum*). GenBank CAB77207.1. 2002. p. 1-2.*
Extended European Search Report for corresponding EP Patent Application No. 09735895.6 issued on Jun. 25, 2012.
Seiichi Taguchi et al: "A microbial factory for lactate-based polyesters using a lactate-polymerizing enzyme", Proceedings of the National Academy of Sciences, National Academy of Sciences, US, vol. 05, No. 45, Nov. 11, 2008, pp. 17323-17327, XP008143036, ISSN: 0027-8424, DOI: 10.1073/PNAS.0805653105.
Christopher T. Nomura et al., "PHA synthase engineering toward superbiocatalysts for custom-made biopolymers", Appl. Microbiol. Biotechnol., 2007, 73: 969-979.
Wei Yuan et al., "Class I and III Polyhydroxyalkanoate Synthases from *Ralstonia eutropha* and *Allochromatium vinosum*: Characterization and Substrate Specificity Studies", Archives of Biochemistry and Biophysics, 2001, 394(1): 87-98.

(Continued)

*Primary Examiner* — David J Steadman
*Assistant Examiner* — Paul Holland
(74) *Attorney, Agent, or Firm* — Sughrue Mion, PLLC

(57) ABSTRACT

The object of the present invention is to provide a method for efficiently producing a polyester copolymer consisting of 3-hydroxybutyrate and lactate via microbial fermentation with the use of a sugar as a starting material. The method may comprise culturing a recombinant microorganism expressing: a protein capable of catalyzing the transfer of CoA to propionic acid and/or lactate; a protein capable of catalyzing the formation of acetoacetyl-CoA from two acetyl-CoA molecules; a protein capable of catalyzing acetoacetyl-CoA reduction; and a protein capable of catalyzing polyhydroxyalkanoate synthesis. According to the production method, a polyester copolymer consisting of 3-hydroxybutyrate and lactate can be efficiently produced using an inexpensive carbon source as a starting material, and thus the production cost of a biodegradable plastic can be reduced.

9 Claims, 35 Drawing Sheets

(56) References Cited

OTHER PUBLICATIONS

Restriction Requirement issued in related U.S. Appl. No. 13/126,157 on Mar. 1, 2013.

Office Action issued in U.S. Appl. No. 13/126,157, dated Jun. 18, 2013.

Selmer et al., Accession No. Q9L3F7, Acetate CoA-transferase YdiF, Database UniProtKB/TrEMBL (online), Oct. 1, 2000, retrieved from http://www.uniprot.org/uniprot/Q9L3F7 on Aug. 28, 2013.

Paulsen, Accession No. B1BAC4, Acetate CoA-transferase YdiF, Database UniProtKB/TrEMBL (online), Apr. 29, 2008, retrieved from http://www.uniprot.org/uniprot/B1BAC4 on Aug. 28, 2013.

Bettegowda et al., Accession No. A0Q1E3, Acetate CoA-transferase YdiF, Database UniProtKB/TrEMBL (online), Jan. 9, 2007, retrieved from http://www.uniprot.org/uniprot/A0Q1E3 on Aug. 28, 2013.

Thorsten Selmer et al., "Propionate CoA-transferase from Clostridium propionicum: Cloning of the gene and identification of glutamate 324 at the active site," Eur. J. Biochem, 2002, 269: 372-380.

S. Sen et al., "Developments in Directed Evolution for Improving Enzyme Functions," Appl. Biochem. Biotechnol., 2007, 143: 212-223.

Roberto A. Chica et al., "Semi-rational approaches to engineering enzyme activity: combining the benefits of directed evolution and rational design," Curr. Opin. Biotech., 2005, 16(4): 378-384.

* cited by examiner

Fig. 10
A
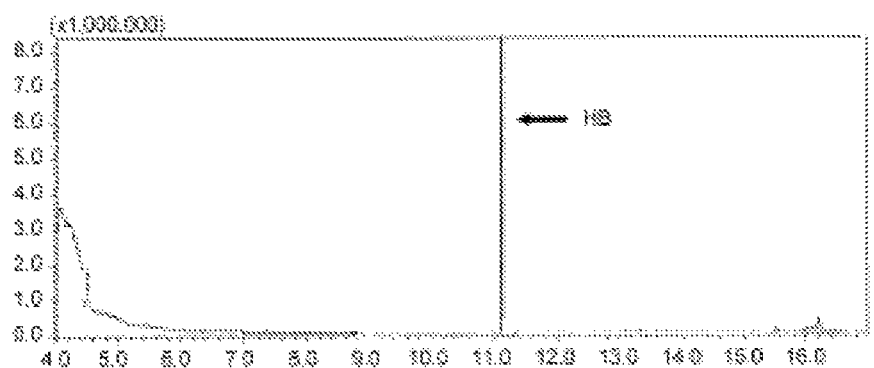
B
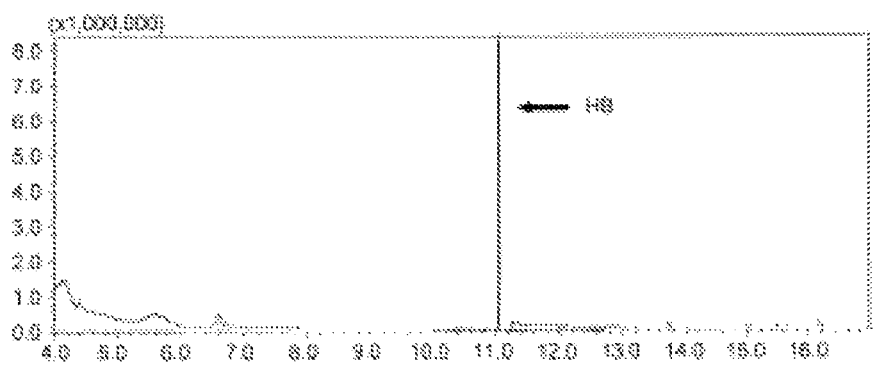
C
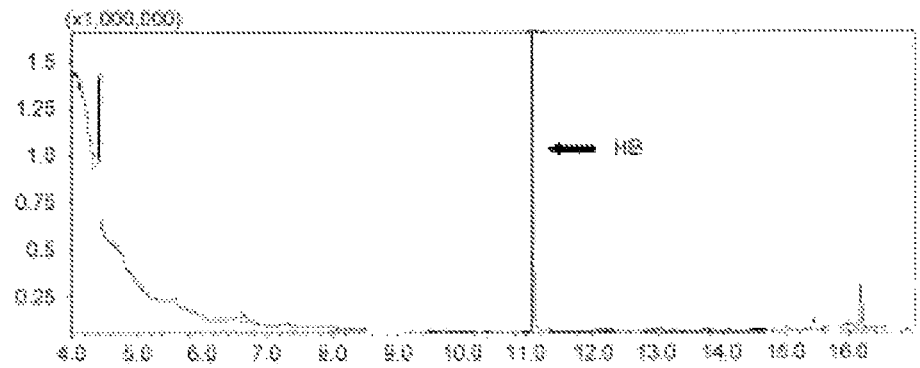

Fig. 1 2 a
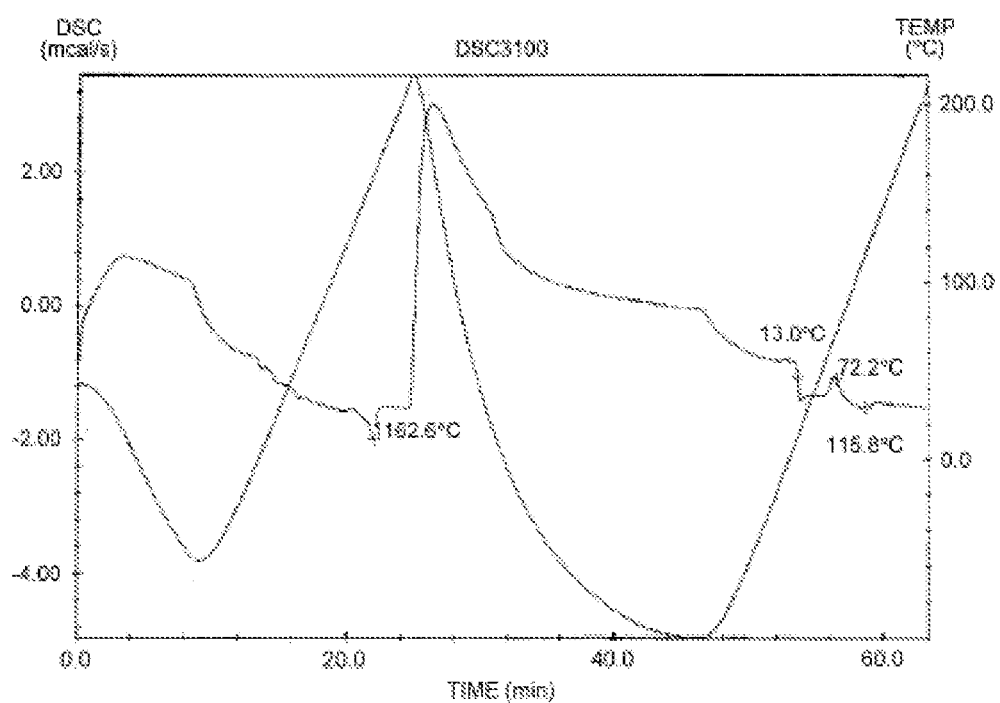

Fig. 1 2 b
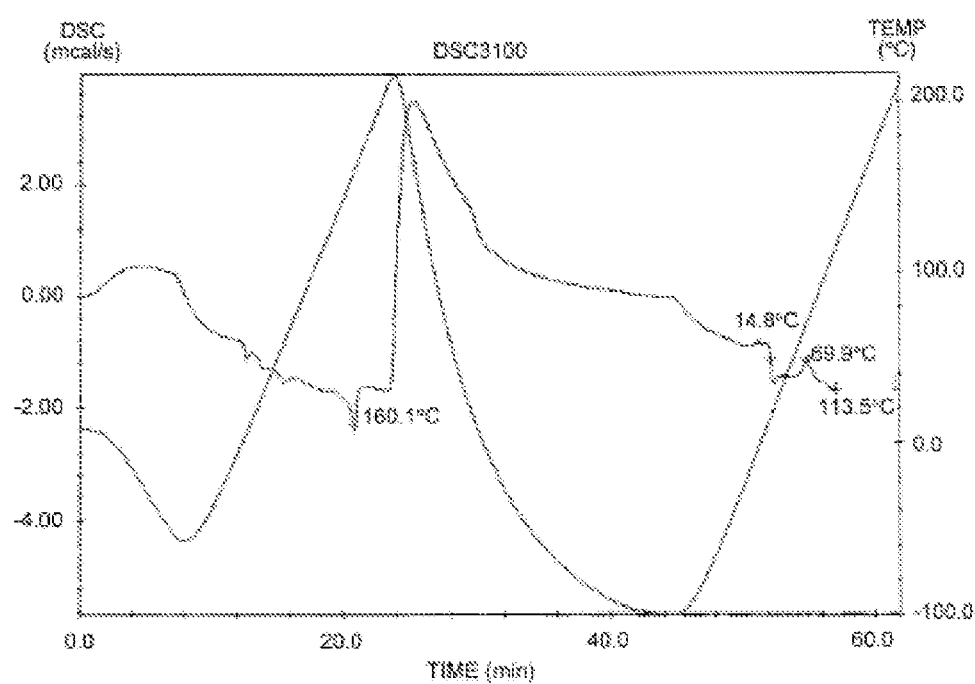

Fig. 1 3 a
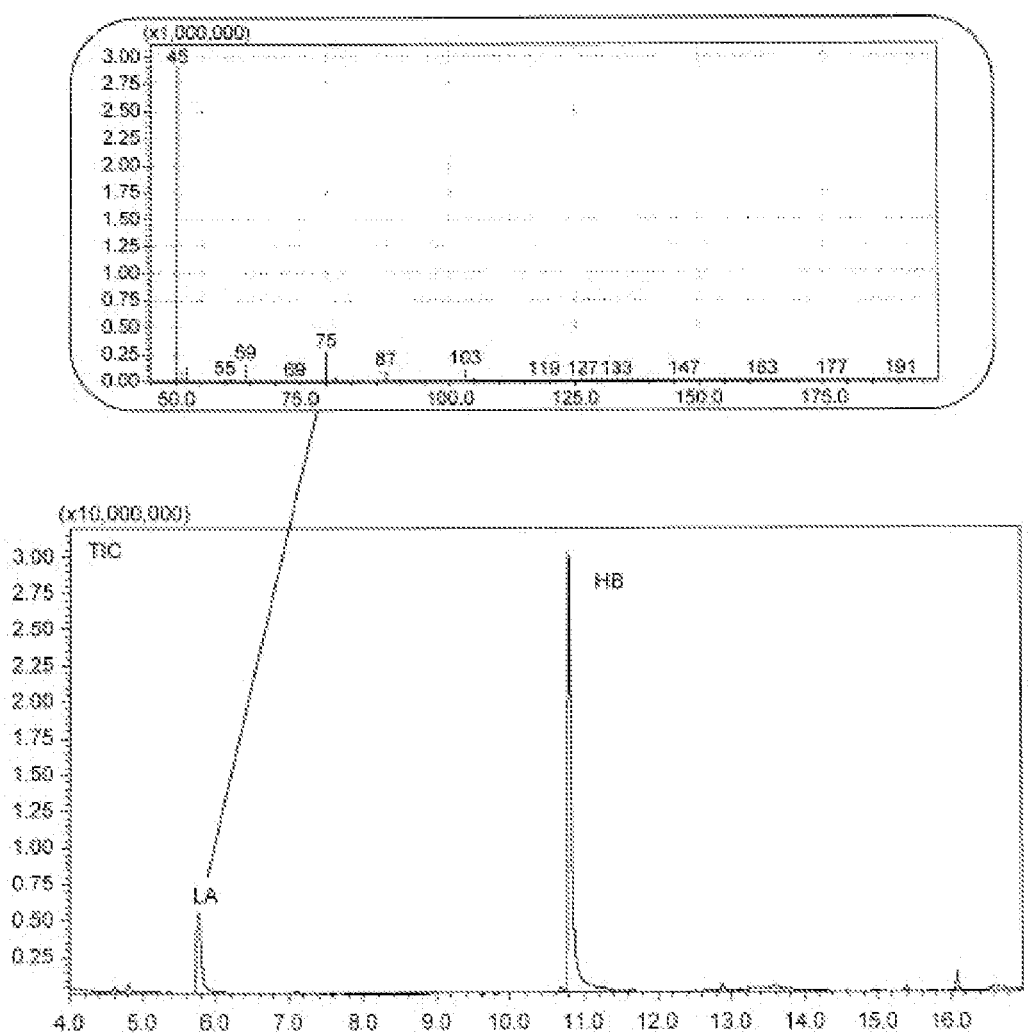

Fig. 1 3 c
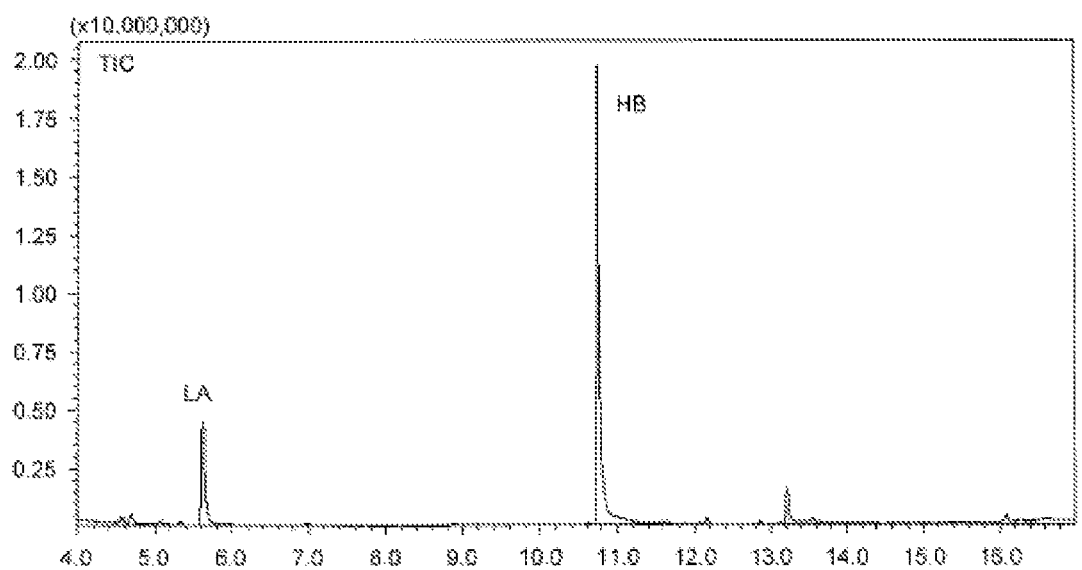

METHOD FOR PRODUCTION OF POLYESTER COPOLYMER USING RECOMBINANT MICROORGANISM

TECHNICAL FIELD

The present invention relates to a method for producing a polyester copolymer using a recombinant microorganism.

BACKGROUND ART

Many microorganisms have been reported to have the ability to produce a polyester using a sugar as a carbon source (Non-Patent Document 1). Polyesters produced by microorganisms have been gaining attention as biodegradable plastics that can be readily degraded in nature or as "green" plastics that can be synthesized from renewable carbon resources such as sugars or plant oils.

A representative example of a biodegradable plastic produced by a microorganism is poly-3-hydroxybutyrate (polyhydroxybutyrate (PHB)) consisting of 3-hydroxybutyrate (3HB) monomers. PHB is a thermoplastic polymer having a melting temperature of approximately 180° C. PHB has excellent melting processability as well as biodegradability, which is advantageous. At the same time, PHB is hard and fragile because of its high crystallinity. That is to say, it has poor shock resistance, which is problematic in terms of physical properties.

As a method for solving problems regarding physical properties of PHB, a method for producing a polyester copolymer consisting of 3HB and a different hydroxyalkanoate using a microorganism has been developed.

For example, Patent Document 1 discloses a method for producing a copolymer consisting of 3HB and 3-hydroxyvalerate (3HV). In addition, Patent Document 2 discloses a method for producing a copolymer consisting of 3HB and 3HV by allowing a microorganism of the genus *Methylobacterium* (*Methylobacterium* sp.), *Paracoccus* (*Paracoccus* sp.), *Alcaligenes* (*Alcaligenes* sp.), or *Pseudomonas* (*Pseudomonas* sp.) to come into contact with a primary alcohol having a carbon number of 3 to 7.

Such copolymer consisting of 3HB and 3HV has a higher degree of flexibility than PHB. In addition, it has been confirmed that an increase in the 3HV content in a polyester copolymer results in enhanced flexibility. In the above method for producing a copolymer consisting of 3HB and 3HV using a microorganism, the 3HV content in a polyester copolymer is regulated by adding, for example, propionic acid in the case of Patent Document 1 or propane-1-ol in the case of Patent Document 3 to a medium.

For instance, P(3HB-co-3HH), which is a two-component polyester copolymer consisting of 3HB and 3-hydroxyhexanoate (hereinafter abbreviated as "3HH"), and a method for producing the same are disclosed in Patent Documents 4 and 5. In the methods for producing a P(3HB-co-3HH) copolymer disclosed in these Patent Documents, fermentative production from a fatty acid such as oleic acid or fat and oil such as olive oil is carried out using *Aeromonas caviae* isolated from the soil. In addition, it has been reported that a recombinant strain is obtained by cloning the PHA synthase gene from *A. caviae* and introducing the cloned gene into *Alcaligenes eutrophus* for production of P(3HB-co-3HH) with the use of fatty acid as a carbon source and the recombinant strain (Patent Document 6).

In addition, in any case of the above methods for producing a polyester copolymer using a microorganism, it is necessary to use a polyhydroxyalkanoate synthase, which is an enzyme protein having activity of directly synthesizing a polymer. In addition, it has been attempted to modify such synthase so as to control the monomer unit mole fraction. For example, Patent Document 7 discloses a mutant enzyme capable of producing PHB with a high 3HB content, which is obtained by modifying the amino acid sequence of a polyhydroxyalkanoate synthase of a microorganism that has been identified as *Pseudomonas* sp. 61-3.

In the above document, a polyester copolymer consisting of 3-hydroxyalkanoate serving as a monomer unit and a method for producing the same using a microorganism are described. Meanwhile, a polyester copolymer consisting of a non-3-hydroxyalkanoate component serving as a monomer unit is expected to have physical properties differing from those of the above polyester copolymer. Patent Document 8 discloses a method for producing, as an example of such polyester copolymer comprising a non-3-hydroxyalkanoate component serving as a monomer unit, a polyester copolymer consisting of 3HB and lactate (LA) by culturing *Ralstonia eutropha* (previous name: *Alcaligenes eutrophus*) incorporating the nucleic acid encoding propionyl-CoA transferase of *Clostridium propionicum* with the addition of lactate to a medium. The document further discloses a method for producing a copolymer consisting of 3-hydroxyhexanoate, 3-hydroxyoctanoate, 3-hydroxydecanoate, and lactate by culturing *Escherichia coli* incorporating the nucleic acid encoding *C. propionium*-derived propionyl-CoA transferase and the nucleic acid encoding *Pseudomonas* sp. 61-3-derived polyhydroxyalkanoate synthase with addition of lactate and decenoic acid to a medium.

However, a method for synthesizing polyhydroxyalkanoate with the addition of a monomer component such as lactate or decenoic acid to a medium is disadvantageous in terms of cost of starting materials. Further, in general, the polymer productivity and the carbon source yield become low in the case of production of a polyester copolymer using a microorganism. Therefore, improvement of productivity or yield is an important task for reduction of production cost also in a case in which an inexpensive natural substance or the like is used as a carbon source.

Non-Patent Document 1: "Biodegradable Plastic Handbook," Biodegradable Plastics Society, 1995, pp. 178-197, published by NTS Inc.)
Patent Document 1: JP Patent Publication (Kokai) No. 57-150393 A (1982)
Patent Document 2: JP Patent Publication (Kokai) No. 5-74492 A (1993)
Patent Document 3: JP Patent Publication (Kokoku) No. 7-79705 B (1995)
Patent Document 4: JP Patent Publication (Kokai) No. 5-93049 A (1993)
Patent Document 5: JP Patent Publication (Kokai) No. 7-265065 A (1995)
Patent Document 6: JP Patent Publication (Kokai) No. 10-108682 A (1998)
Patent Document 7: WO2003/100055
Patent Document 8: WO2006/126796

DISCLOSURE OF THE INVENTION

Problem to be Solved by the Invention

It is an object of the present invention to provide a method for efficiently producing a polyester copolymer consisting of 3HB and LA (other than 3-hydroxyalkanoate) serving as a monomer unit via microbial fermentation with the use of a sugar as a starting material. In addition, it is another object of the present invention to provide a method for producing a polyester copolymer containing LA at a different mole fraction by regulating the 3HB mole fraction in a polyester depending on the characteristics of an enzyme to be used, selecting a specific host, or adjusting culture conditions. It is a further object of the present invention to provide a method for efficiently producing a polyester copolymer further comprising a monomer unit other than LA and 3HB via microbial fermentation with the use of a sugar as a starting material.

Means for Solving Problem

The present inventors found that a recombinant microorganism into which the nucleic acid encoding the polyhydroxyalkanoate synthase mutant disclosed in Patent Document 7 has been introduced can efficiently produce a polyester copolymer consisting of 3HB and LA directly from a sugar, and that the LA mole fraction in the copolymer can be controlled. The present inventors further found that a polyester copolymer further comprising a monomer unit other than LA and 3HB can be efficiently produced by supplying a precursor of the monomer component other than 3HB or LA to a medium. This has led to the completion of the individual inventions described below.

(1) A method for producing a polyester copolymer consisting of 3-hydroxybutyrate and lactate, which comprises the steps of:

1) culturing a recombinant microorganism having a protein capable of catalyzing a reaction of transferring CoA to propionic acid and/or lactate, a protein capable of catalyzing a reaction of forming acetoacetyl-CoA from two acetyl-CoA molecules, a protein capable of catalyzing a reaction of acetoacetyl-CoA reduction, and a protein capable of catalyzing a reaction of polyhydroxyalkanoate synthesis consisting of the following amino acid sequence (a) or (b) in a medium containing a carbon source:

(a) an amino acid sequence derived from the amino acid sequence shown in SEQ ID NO: 2 by substitution of at least one of the amino acids at positions 130, 325, 477, and 481 with different amino acid(s); or (b) an amino acid sequence derived from the protein specified in (a) by additional deletion or substitution of at least one amino acid other than the amino acids at positions 130, 325, 477, and 481 or by insertion of at least one amino acid residue; and 2) collecting the polyester copolymer from the culture product obtained in step 1).

(2) The production method according to (1), wherein the amino acid sequence of the protein capable of catalyzing a reaction of transferring CoA to propionic acid and/or lactate is the amino acid sequence shown in SEQ ID NO: 4 or an amino acid sequence derived from the amino acid sequence shown in SEQ ID NO: 4 by deletion, substitution, or addition of one or more amino acid(s).

(3) The production method according to (1), wherein the amino acid sequence of the protein capable of catalyzing a reaction of forming acetoacetyl-CoA from two acetyl-CoA molecules is the amino acid sequence shown in SEQ ID NO: 6 or an amino acid sequence derived from the amino acid sequence shown in SEQ ID NO: 6 by deletion, substitution, or addition of one or more amino acid(s).

(4) The production method according to (1), wherein the amino acid sequence of the protein capable of catalyzing a reaction of acetoacetyl-CoA reduction is the amino acid sequence shown in SEQ ID NO: 8 or an amino acid sequence derived from the amino acid sequence shown in SEQ ID NO: 8 by deletion, substitution, or addition of one or more amino acid(s).

(5) The production method according to (1), wherein the amino acid sequence of the protein capable of catalyzing a reaction of polyhydroxyalkanoate synthesis is an amino acid sequence derived from the amino acid sequence shown in SEQ ID NO: 2 by substitution of amino acids at positions 325 and 481 with different amino acids.

(6) The production method according to (5), wherein the amino acid sequence of the protein capable of catalyzing a reaction of polyhydroxyalkanoate synthesis is an amino acid sequence derived from the amino acid sequence shown in SEQ ID NO: 2 by simultaneous substitution of amino acids at positions 325 and 481.

(7) The production method according to (6), wherein the amino acid sequence of the protein capable of catalyzing a reaction of polyhydroxyalkanoate synthesis is an amino acid sequence derived from the amino acid sequence shown in SEQ ID NO: 2 by substitution of Ser at position 325 with Thr and Gln at position 481 with Lys.

(8) The production method according to (1), wherein any one of the proteins is a protein encoded by a recombinant expression vector introduced into a microorganism.

(9) The production method according to any one of (1) to (8), wherein culture of the recombinant microorganism is carried out under anaerobic conditions.

(10) The production method according to any one of (1) to (9), wherein the microorganism is a microorganism having the ability to accumulate lactate.

(11) The production method according to (10), wherein the microorganism having a high degree of ability to accumulate lactate is of the *Escherichia coli* Jw2293, Jw0885, or Jw0886 strain.

(12) A method for producing a polyester copolymer consisting of 3-hydroxybutyrate and lactate, which comprises the steps of:

1) culturing a recombinant microorganism having a protein capable of catalyzing a reaction of transferring CoA to propionic acid and/or lactate, a protein capable of catalyzing a reaction of forming acetoacetyl-CoA from two acetyl-CoA molecules, a protein capable of catalyzing a reaction of acetoacetyl-CoA reduction, and a protein capable of catalyzing a reaction of polyhydroxyalkanoate synthesis consisting of the following amino acid sequence (a) or (b) in a medium containing a hydroxyalkanoate other than 3-hydroxybutyrate and lactate and a carbon source:

(a) an amino acid sequence derived from the amino acid sequence shown in SEQ ID NO: 2 by substitution of at least one of the amino acids at positions 130, 325, 477, and 481 with different amino acid(s); or (b) an amino acid sequence derived from the protein specified in (a) by additional deletion or substitution of at least one amino acid other than the amino acids at positions 130, 325, 477, and 481 or by insertion of at least one amino acid residue; and 2) collecting the polyester copolymer from the culture product obtained in step 1).

(13) The production method according to (12), wherein the amino acid sequence of the protein capable of catalyzing a reaction of transferring CoA to propionic acid and/or lactate is the amino acid sequence shown in SEQ ID NO: 4 or an amino acid sequence derived from the amino acid sequence shown in SEQ ID NO: 4 by deletion, substitution, or addition of one or more amino acid(s).

(14) The production method according to (12), wherein the amino acid sequence of the protein capable of catalyzing a reaction of forming acetoacetyl-CoA from two acetyl-CoA molecules is the amino acid sequence shown in SEQ ID NO: 6 or an amino acid sequence derived from the amino acid sequence shown in SEQ ID NO: 6 by deletion, substitution, or addition of one or more amino acid(s).

(15) The production method according to (12), wherein the amino acid sequence of the protein capable of catalyzing a reaction of acetoacetyl-CoA reduction is the amino acid sequence shown in SEQ ID NO: 8 or an amino acid sequence derived from the amino acid sequence shown in SEQ ID NO: 8 by deletion, substitution, or addition of one or more amino acid(s).

(16) The production method according to (12), wherein the amino acid sequence of the protein capable of catalyzing a reaction of polyhydroxyalkanoate synthesis is an amino acid sequence derived from the amino acid sequence shown in SEQ ID NO: 2 by substitution of amino acids at positions 325 and 481 with different amino acids.

(17) The production method according to (12), wherein the amino acid sequence of the protein capable of catalyzing a reaction of polyhydroxyalkanoate synthesis is an amino acid sequence derived from the amino acid sequence shown in SEQ ID NO: 2 by simultaneous substitution of amino acids at positions 325 and 481.

(18) The production method according to (16) or (17), wherein the amino acid sequence of a protein capable of catalyzing a reaction of polyhydroxyalkanoate synthesis is an amino acid sequence derived from the amino acid sequence shown in SEQ ID NO: 2 by substitution of Ser at position 325 with Thr and Gln at position 481 with Lys.

(19) The production method according to (12), wherein any one of the proteins is a protein encoded by a recombinant expression vector introduced into a microorganism.

(20) The production method according to any one of (12) to (19), wherein a precursor of the hydroxyalkanoate other than 3-hydroxybutyrate or lactate is at least one precursor selected from the group consisting of propionic acid, valeric acid, dodecanoic acid, 4-hydroxybutanoate, and 4-hydroxyvalerate.

(21) The production method according to any one of (12) to (20), wherein the culture of a recombinant microorganism is carried out under anaerobic conditions.

(22) The production method according to any one of (12) to (21), wherein the microorganism is a microorganism having the ability to accumulate lactate.

(23) The production method according to (22), wherein the microorganism having a high degree of ability to accumulate lactate is of the *Escherichia coli* Jw2293, Jw0885, or Jw0886 strain.

(24) A recombinant microorganism that expresses a protein capable of catalyzing a reaction of transferring CoA to propionic acid and/or lactate, a protein capable of catalyzing a reaction of forming acetoacetyl-CoA from two acetyl-CoA molecules, a protein capable of catalyzing a reaction of acetoacetyl-CoA reduction, and a protein capable of catalyzing a reaction of polyhydroxyalkanoate synthesis consisting of the following amino acid sequence (a) or (b):

(a) an amino acid sequence derived from the amino acid sequence shown in SEQ ID NO: 2 by substitution of at least one of the amino acids at positions 130, 325, 477, and 481 with different amino acid(s); or (b) an amino acid sequence derived from the protein specified in (a) by additional deletion or substitution of at least one amino acid other than the amino acids at positions 130, 325, 477, and 481 or by insertion of at least one amino acid residue.

(25) The recombinant microorganism according to (24), wherein the amino acid sequence of the protein capable of catalyzing a reaction of transferring CoA to propionic acid and/or lactate is the amino acid sequence shown in SEQ ID NO: 4 or an amino acid sequence derived from the amino acid sequence shown in SEQ ID NO: 4 by deletion, substitution, or addition of one or more amino acid(s).

(26) The recombinant microorganism according to (24), wherein the amino acid sequence of the protein capable of catalyzing a reaction of forming acetoacetyl-CoA from two acetyl-CoA molecules is the amino acid sequence shown in SEQ ID NO: 6 or an amino acid sequence derived from the amino acid sequence shown in SEQ ID NO: 6 by deletion, substitution, or addition of one or more amino acid(s).

(27) The recombinant microorganism according to (24), wherein the amino acid sequence of the protein capable of catalyzing a reaction of acetoacetyl-CoA reduction is the amino acid sequence shown in SEQ ID NO: 8 or an amino acid sequence derived from the amino acid sequence shown in SEQ ID NO: 8 by deletion, substitution, or addition of one or more amino acid(s).

(28) The recombinant microorganism according to (24), wherein the amino acid sequence of the protein capable of catalyzing a reaction of polyhydroxyalkanoate synthesis is an amino acid sequence derived from the amino acid sequence shown in SEQ ID NO: 2 by substitution of amino acids at positions 325 and 481 with different amino acids.

(29) The recombinant microorganism according to (24), wherein the amino acid sequence of the protein capable of catalyzing a reaction of polyhydroxyalkanoate synthesis is an amino acid sequence derived from the amino acid sequence shown in SEQ ID NO: 2 by simultaneous substitution of amino acids at positions 325 and 481.

(30) The recombinant microorganism according to (28) or (29), wherein the amino acid sequence of a protein capable of catalyzing a reaction of polyhydroxyalkanoate synthesis is an amino acid sequence derived from the amino acid sequence shown in SEQ ID NO: 2 by substitution of Ser at position 325 with Thr and Gln at position 481 with Lys.

(31) The recombinant microorganism according to (24), wherein any one of the proteins is a protein encoded by a recombinant expression vector introduced into a microorganism.

(32) The recombinant microorganism according to any one of (24) to (31), wherein the microorganism is a microorganism having the ability to accumulate lactate.

(33) The recombinant microorganism according to (32), wherein the microorganism having a high degree of ability to accumulate lactate is of the *Escherichia coli* Jw2293, Jw0885, or Jw0886 strain.

Effects of the Invention

According to the production method of the present invention, a polyester copolymer consisting of 3HB and LA can be efficiently produced using an inexpensive carbon source as a starting material, and thus the production cost of a biodegradable plastic can be reduced. In addition, the monomer unit content of a polyester copolymer consisting of 3HB and LA can be controlled by selecting an enzyme to be used, using a microorganism capable of high LA production as a host, or carrying out microbial culture under anaerobic conditions. In addition, a polyester copolymer further comprising a monomer unit other than 3HB or LA can be produced by adding a hydroxyalkanoate other than 3HB or LA to a medium.

This description includes part or all of the contents as disclosed in the descriptions and/or drawings of Japanese Patent Application Nos. 2008-113127 and 2008-298765 which are priority documents of the present application.

BRIEF DESCRIPTION OF THE DRAWINGS

FIG. 10 shows charts indicating GC/MS analysis results for the polymers from pTV118NPCTC(Re)AB and pTV118NPCTC(Bc) prepared in the Comparative Example. Panel A is a chart for pTV118NPCTC(Re)AB, panel B is a chart for pTV118NPCTC(Bc), and panel C is a chart for pTV118NPCTC2AB.

FIG. 12*a* is a graph showing thermal analysis measurement results for the polymer from the *Escherichia coli* Jw2293 strain capable of high LA accumulation prepared in Example 2.

FIG. 12*b* is a graph showing thermal analysis measurement results for the polymer from the *Escherichia coli* Jw0885 strain capable of high LA accumulation prepared in Example 2.

FIG. 13*a* is a chart showing GC/MS analysis results for the polymer from the *Escherichia coli* Jw2293 strain capable of high LA accumulation prepared in Example 2.

FIG. 13*c* is a chart showing GC/MS analysis results for the polymer from the *Escherichia coli* Jw0886 strain capable of high LA accumulation prepared in Example 2.

FIG. 22 is a chart showing $^1$H$^{13}$C-NMR spectral analysis results for the polymer prepared in Example 3.

FIG. 25 shows an HPLC chart for a polymer obtained in Example 4.

Figure 1:
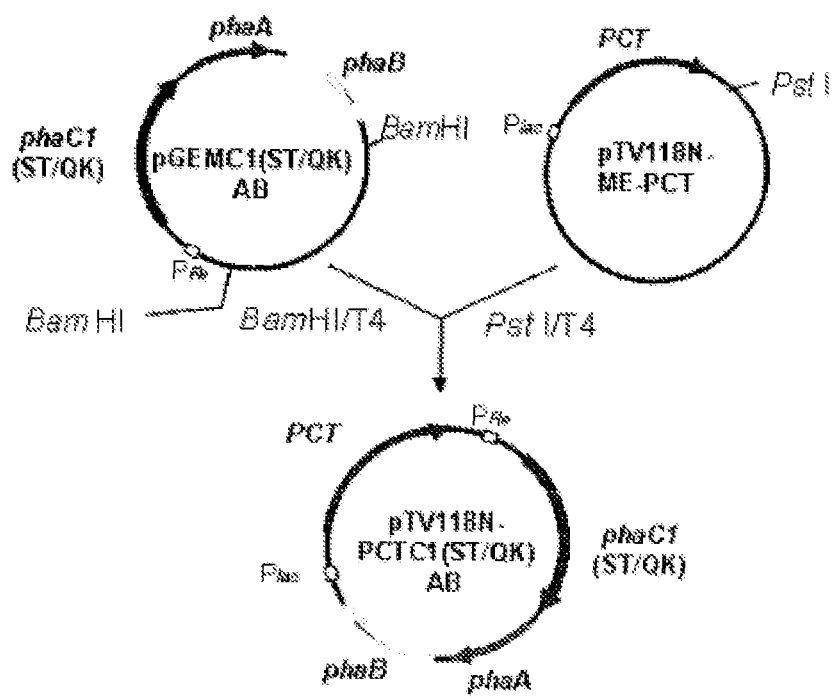
FIG. 1 schematically shows the configuration of a recombinant plasmid pTV118NPCTC1(ST/QK)AB. In the figure, "phaA" denotes an *R. eutropha*-derived β KT gene, "phaB" denotes an *R. eutropha*-derived AACoA-R gene, "phaC1(ST/QK)" denotes the STQK gene, "PCT" denotes the *M. elsdenii*-derived pct gene, "PRe" denotes an *R. eutropha*-derived promoter, and "Plac" denotes an *Escherichia coli* lactose operon promoter.

EXPLANATION OF ABBREVIATIONS phaA: *R. eutropha*-derived β KT gene
phaB: *R. eutropha*-derived AACoA-R gene
phaC(Re): *R. eutropha*-derived polyhydroxyalkanoate synthase gene
phaC(Bc): *B. cereus*-derived polyhydroxyalkanoate synthase gene
phaC1(WT): *Pseudomonas* sp. 61-3-derived polyhydroxyalkanoate synthase gene (wild-type)
phaC2: *Pseudomonas* sp. 61-3-derived polyhydroxyalkanoate synthase 2 gene
PCT: *M. elsdenii*-derived pct gene
PRe: *Alcaligenes eutrophus*-derived promoter
Plac: Lactose operon promoter

BEST MODE FOR CARRYING OUT THE INVENTION

The present invention relates to a method for producing a polyester copolymer consisting of 3HB and LA, which comprises the steps of:

(1) culturing a recombinant microorganism having a protein capable of catalyzing a reaction of transferring CoA to propionic acid and/or lactate, a protein capable of catalyzing a reaction of forming acetoacetyl-CoA from two acetyl-CoA molecules, a protein capable of catalyzing a reaction of acetoacetyl-CoA reduction, and a protein capable of catalyzing a reaction of polyhydroxyalkanoate synthesis consisting of the following amino acid sequence (a) or (b) in a medium containing a carbon source:

(a) an amino acid sequence derived from the amino acid sequence shown in SEQ ID NO: 2 by substitution of at least one of the amino acids at positions 130, 325, 477, and 481 with different amino acid(s); or (b) an amino acid sequence derived from the protein specified in (a) by additional deletion or substitution of at least one amino acid other than the amino acids at positions 130, 325, 477, and 481 or by insertion of at least one amino acid residue; and (2) collecting the polyester copolymer from the culture product obtained in step (1). Hereinafter, proteins and recombinant microorganisms used in the present invention and conditions for the production method of the present invention are described.

(1) A Protein Capable of Catalyzing a Reaction of Transferring CoA to Propionic Acid and/or Lactate (LA)

A "protein capable of catalyzing a reaction of transferring CoA to propionic acid and/or LA" used in the present invention is a protein having activity of catalyzing a reaction of transferring CoA from an appropriate CoA substrate to propionic acid and/or LA. The protein having such activity is generally referred to as propionyl-CoA transferase (pct). Hereinafter, the protein is denoted by "pct" in the present invention.

Table 1 shows representative examples of pct origins (microorganism names) that have been reported in the past and information on references disclosing the nucleotide sequences encoding the microorganisms.

TABLE 1

| Microorganism name | Reference information |
|---|---|
| Clostridium propionicum | Eur. J. Biochem., 2002, Vol. 269, pp. 372-380 |
| Megasphaera elsdenii | U.S. Pat. No. 7,186,541 |
| Staphylococcus aureus | Eur. J. Biochem., 2002, Vol. 269, pp. 372-380 |
| Escherichia coli | Eur. J. Biochem., 2002, Vol. 269, pp. 372-380 |

In addition to the above examples shown in table 1, any pct that has been reported in the past can be used in the present invention. In addition, as long as a "protein capable of catalyzing a reaction of transferring CoA to propionic acid and/or LA" is used, even a protein consisting of an amino acid sequence derived from the amino acid sequence of a known pct by deletion, substitution, or addition of 1 or more (for example, 1 to several tens of, preferably 1 to less than 20, and more preferably not more than 10 amino acid(s) can be used.

Catalytic activity in a reaction of transferring CoA to propionic acid and/or LA can be determined according to, for example, the method described by A. E. Hofmeister et al. (Eur. J. Biochem., vol. 206, pp. 547-552).

A preferable example of pct in the present invention is *Megasphaera elsdenii*-derived pct. The amino acid sequence thereof is shown in SEQ ID NO: 4. An example of the nucleotide sequence of nucleic acid (DNA) encoding the amino acid sequence is shown in SEQ ID NO: 3.

(2) A Protein Capable of Catalyzing a Reaction of Forming Acetoacetyl-CoA from Two Acetyl-CoA Molecules The "protein capable of catalyzing a reaction of forming acetoacetyl-CoA from two acetyl-CoA molecules" used in the present invention is a protein capable of catalyzing a reaction that causes condensation of two acetyl-CoA molecules to result in formation of acetoacetyl-CoA. In general, the protein is referred to as "β ketothiolase" or "acetyl-CoA-CoA-C-acetyltransferase." Hereinafter, according to the present invention, a "protein capable of catalyzing a reaction of forming acetoacetyl-CoA from two acetyl-CoA molecules" is referred to as "β KT."

Table 2 shows representative examples of β KT origins (microorganism names) that have been reported in the past and information on references disclosing the nucleotide sequences encoding the microorganisms.

TABLE 2

| Microorganism name | Reference information |
|---|---|
| Alkaligenes beijerinckii | Biochem. J., 1973, Vol. 134, pp. 225-238 |
| R. eutropha | Biochem. J., 1973, Vol. 134, pp. 239-248 |
| Clostridium pasteurianum | Arch. Microbiol., 1975, Vol. 103, pp. 21-30 |
| Z. ramigera | U.S. Pat. No. 067,695 |

In addition to the above examples shown in table 2, any β KT that has been reported in the past can be used in the present invention. In addition, as long as a "protein capable of catalyzing a reaction of forming acetoacetyl-CoA from two acetyl-CoA molecules" is used, even a protein consisting of an amino acid sequence derived from the amino acid sequence of a known β KT by deletion, substitution, or addition of 1 or more (for example, 1 to several tens of, preferably 1 to less than 20, and more preferably not more than 10) amino acid(s) can be used.

Catalytic activity for a reaction of forming acetoacetyl-CoA from two acetyl-CoA molecules can be determined by the method described by, for example, Slater et al. (J. Bacteriology, 1998, vol. 180, pp. 1979-1987).

A preferable example of β KT in the present invention is *R. eutropha*-derived β KT. The amino acid sequence thereof is shown in SEQ ID NO: 6. An example of the nucleotide sequence of nucleic acid (DNA) encoding the amino acid sequence is shown in SEQ ID NO: 5.

(3) A Protein Capable of Catalyzing a Reaction of Acetoacetyl-CoA Reduction

The "protein capable of catalyzing a reaction of acetoacetyl-CoA reduction" used in the present invention is a protein capable of catalyzing a reaction that causes formation of D(−)-β-hydroxybutyryl-CoA via reduction reaction that takes place in the presence of an acetoacetyl-CoA coenzyme such as NADP. In general, the "protein capable of catalyzing a reaction of acetoacetyl-CoA reduction" is referred to as "AACoA-R."

Table 3 shows examples of AACoA-R origins (microorganism names) that have been reported in the past and information on references disclosing the nucleotide sequences encoding the microorganisms or the database registration number.

TABLE 3

| Microorganism name | Reference information or database registration number |
|---|---|
| Zoogloea | Arch. Microbiol., 1977, Vol. 114, pp. 211-217 |
| R. eutropha | Accession No. J04987 |
| Z. ramigera | U.S. Pat. No. 067,695 |

In addition to the above examples shown in table 3, any AACoA-R that has been reported in the past can be used in the present invention. In addition, as long as a "protein capable of catalyzing a reaction of acetoacetyl-CoA reduction" is used, even a protein consisting of an amino acid sequence derived from the amino acid sequence of a known AACoA-R by deletion, substitution, or addition of 1 or more (for example, 1 to several tens of, preferably 1 to less than 20, and more preferably not more than 10) amino acid(s) can be used.

Catalytic activity for a reaction of acetoacetyl-CoA reduction can be determined by, for example, the method described by G. W. Haywood et al. (FEMS Microbiology Letters, 1988, vol. 52, pp. 259-264).

A preferable example of AACoA-R in the present invention is *R. eutropha*-derived AACoA-R. The amino acid sequence thereof is shown in SEQ ID NO: 8. An example of the nucleotide sequence of nucleic acid (DNA) encoding the amino acid sequence is shown in SEQ ID NO: 7.

In addition, table 4 lists known examples of β KT and AACo-R and the accession numbers thereof.

TABLE 4

| Designation | Organism | Accession No. |
|---|---|---|
| phaBPCA | *Acinetobacter* sp. RA3849 | L37761 |
| phaPCJ | *Aeromonas caviae* FA440 | D88825 |
| phaCAB | *Alcaligenes laatus* DSM1123 | AF078795 |
| phaCAB | *Alcaligenes laatus* DSM1124 | U47026 |
| phaA | *Alcaligenes* sp. SH-69 | AF002013 |
| phaBPCA | *Alcaligenes* sp. SH-69 | AF002014 |
| phaCEARPB | *Allochromatium vinosum* D | L01112 |
| phaPBC | *Bacillus megaterium* ATCC11561 | AF109909 |
| phaCABR | *Burkholderia* sp. DSM 9242 | AF153086 |
| phaCA | *Chromobacterium violaceum* DSM30191 | AF061446 |
| phaCA | *Comamonas acidovorans* DS-17 | AB009273 |
| phaCEAPB | *Ectothiorhodospira shaposhnikovii* | AF307334 |
| phaAB | *Paracoccus denitrificans* | D49326 |
| phaCABR | *Pseudomonas acidophila* | — |
| phbRBAC | *Pseudomonas* sp. 61-3 | AB014757 |
| phaAB | *Ralstonia eutropha* H16 | J04987 |
| phaCA, phaC, phaB | *Rrickettsia prowazedkii* Madrid E | AJ235273 |
| phaAB | *Sinorhizobium meliloti* | U17226 |
| phaC | *Sinorhizobium meliloti* Rm1021 | AF031938 |
| phaCE | *Sunechocystis* sp. PCC6803 | D90906 |
| phaAB | *Sunechocystis* sp. PCC6803 | D90910 |
| phaCE | *Thiococcus pfennigii* | A49465 |
| phaCE | *Thiocystis violacea* 2311 | L01113 |
| phaBAPC | *Vibrio cholerae* | AE004398 |
| phaA(B) | *Zoogloea ramigera* | J02631 |

(4) A Protein Capable of Catalyzing a Reaction of Polyhydroxyalkanoate Synthesis The protein capable of catalyzing polyhydroxyalkanoate synthesis of the present invention is a protein consisting of:

(a) an amino acid sequence derived from the amino acid sequence shown in SEQ ID NO: 2 by substitution of at least one of amino acids at positions 130, 325, 477, and 481 with different amino acid(s); or (b) an amino acid sequence derived from the protein specified in (a) by additional deletion or substitution of at least one amino acid other than the amino acids at positions 130, 325, 477, and 481 or by insertion of at least one amino acid residue. This protein is obtained by partially mutating the amino acid sequence of *Pseudomonas* species (*Pseudomonas* sp.) 61-3-derived polyhydroxyalkanoate synthase described in Patent Document 7. Hereinafter, a protein capable of catalyzing polyhydroxyalkanoate synthesis of the present invention is referred to as "PhaCm." In addition, Patent Document 7 is incorporated herein by reference in its entirety.

Preferable examples of PhaCm include a single mutant protein obtained by substitution of any one of the amino acids at positions 130, 325, 477, and 481 of the amino acid sequence shown in SEQ ID NO: 2 listed in table 6 or 7 in Patent Document 7, a double mutant protein obtained by substitution of any two of the same, a triple mutant protein obtained by substitution of any three of the same, and a quadruple mutant protein obtained by substitution of all four of the same. A preferable protein is a double mutant protein obtained by substitution of any two of the above. A particularly preferable protein is a double mutant protein obtained by substitution of Ser at position 325 with Thr and Gln at position 481 with Lys (hereinafter abbreviated as "STQK").

DNA encoding PhaCm can be produced via recombination by a site-specific mutagenesis method known to persons skilled in the art based on the amino acid sequence (SEQ ID NO: 2) of a polyhydroxyalkanoate synthase from *Pseudomonas* species (*Pseudomonas* sp.) 61-3 and the nucleotide sequence (SEQ ID NO: 1) of DNA encoding the same. In addition, as described in Patent Document 7, the PhaCm activity of catalyzing polyhydroxyalkanoate synthesis can be confirmed by obtaining a host cell via transformation with the above nucleic acid capable of expressing PhaCm and examining the polyhydroxyalkanoate accumulation capacity of the host cell.

The 3HB content in a polyester copolymer to be produced can be controlled by selecting and using a different type of PhaCm. For instance, in a case in which STQK described above is used, a random copolymer into which lactate has been randomly incorporated (3HB:lactate=94:6) is produced.

Also, in addition to the selection of PhaCm, the LA mole fraction in a polyester copolymer to be produced can be increased using a microorganism capable of high lactate accumulation such as the *Escherichia coli* Jw2293, Jw0885, or Jw0886 strain as a host. For instance, if an aforementioned *Escherichia coli* strain capable of high lactate accumulation is cultured as a host under aerobic conditions, the LA mole fraction in a polyester copolymer can be increased to approximately 30%.

Further, the LA mole fraction in a polyester copolymer can be increased to a greater extent by devising a way of increasing the LA production with the use of a microorganism. For instance, a host microorganism transformed by the gene encoding the above protein is cultured under anaerobic conditions such that the LA production of the host microorganism itself can be increased. Accordingly, the LA mole fraction in a polyester copolymer to be produced can be increased. The LA mole fraction in a polyester copolymer can be increased to approximately 50% by culturing *Escherichia coli* serving as a host under anaerobic conditions.

(5) Nucleic Acids Encoding the Proteins

The nucleic acids encoding proteins (1) to (4) described above are introduced into microorganisms, followed by protein transcription and translation therein. The thus obtained proteins are preferably used. Each nucleic acid to be introduced into a microorganism is preferably incorporated into a vector.

A vector for introducing the aforementioned nucleic acid into a microorganism may be a vector that can autonomously replicate in a host. Preferable examples thereof include plasmid DNA and phage DNA. Examples of a vector for introducing a nucleic acid into *Escherichia coli* include: plasmid DNAs such as pBR322, pUC18, and pBLuescriptII; and phage DNAs such as EMBL3, M13, and λgtII. In addition, examples of a vector used for introduction into yeast include YEp13 and YCp50.

In addition, examples of a vector used for introduction of a nucleic acid into a microorganism of the genus *Ralstonia* or *Pseudomonas* include pLA2917(ATCC37355) having an RK2 replication origin and pJRD215 (ATCC 37533) having an RSF1010 replication origin, which can be replicated/conserved in a wide range of hosts.

The nucleic acids (preferably DNAs) encoding proteins (1) to (4) described above can be inserted into vectors by a gene recombination technique known to persons skilled in the art. In addition, upon recombination, it is preferable to ligate DNA (inserted into a vector) downstream of a promoter that can control transcription/translation of a relevant protein from the DNA. Any promoter can be used as long as it can control gene transcription in a host. For instance, when *Escherichia coli* is used as a host, a trp promoter, a lac promoter, a PL promoter, a PR promoter, a T7 promoter, or the like can be used. In addition, when yeast is used as a host, a gal1 promoter, a gal10 promoter, or the like can be used. Further, when a microorganism of the genus *Pseudomonas* is used as the microorganism of the present invention, a region such as the region that is supposed to contain a promoter located upstream of the phaC1Ps gene or the phbCABRe operon can be used as a promoter.

In addition, if necessary, the vector of the present invention can be ligated to a terminator sequence, an enhancer sequence, a splicing signal sequence, a polyA addition signal sequence, a ribosome binding sequence (SD sequence), and a selection marker gene, which can be used in a microorganism into which a nucleic acid is introduced. Examples of a selection marker gene include: a gene involved in intracellular biosynthesis of a nutrient such as an amino acid or a nucleic acid and a gene encoding a fluorescent protein such as luciferase, in addition to a drug-resistant gene such as an ampicillin-resistant gene, a tetracycline-resistant gene, a neomycin-resistant gene, a kanamycin-resistant gene, or a chloramphenicol-resistant gene.

Any aforementioned nucleic acid, which is preferably incorporated into a vector, is introduced into a microorganism by a method known to persons skilled in the art. Examples of a method for recombination of a vector into a microorganism include a calcium phosphate method, an electroporation method, a spheroplast method, a lithium acetate method, a conjugational transfer method, and a method using calcium ions.

(6) Microorganism

The recombinant microorganism of the present invention is a microorganism expressing proteins (1) to (4) described above, and it is preferably a microorganism transformed via introduction of the nucleic acids capable of functionally expressing proteins (1) to (4). Preferable examples of such microorganism include bacteria of the genus *Pseudomonas* such as the *Pseudomonas* sp. 61-3 strain, bacteria of the genus *Ralstonia* such as *R. eutropha*, bacteria of the genus *Bacillus* such as *Bacillus subtilis*, bacteria of the genus *Escherichia* such as *Escherichia coli*, bacteria of the genus *Corynebacterium*, yeasts of the genus *Saccharomyces* such as *Saccharomyces cerevisiae*, and yeasts of the genus *Candida* such as *Candida maltosa*. Of these, *Escherichia coli*, bacteria of the genus *Corynebacterium*, and *R. eutropha* are preferable. *Escherichia coli* and bacteria of the genus *Corynebacterium* are particularly preferable.

In the case of a microorganism such as *R. eutropha*, which originally contains a unique polyhydroxyalkanoate synthase, a microorganism lacking the capacity to express such unique polyhydroxyalkanoate synthase is preferably used. Such microorganism lacking expression capacity can be produced by treating a microorganism with a chemical mutation source such as nitrosoguanidine or a physical mutation source such as UV radiation, introducing a mutant nucleic acid (obtained by modifying a nucleic acid encoding a polyhydroxyalkanoate synthase so as not to cause the functional expression of the enzyme) into a microorganism, or inducing "homologous recombination." Destruction of the polyhydroxyalkanoate synthase gene can be confirmed by examining whether a hybridizing band shifts to the expected position when compared with a wild-type strain-derived band upon Southern hybridization with the use of a portion of the gene as a probe.

(6) Production of a Polyester Copolymer Consisting of Hydroxybutyrate and Lactate A polyester copolymer consisting of hydroxybutyrate and lactate can be produced by culturing a recombinant microorganism into which any aforementioned nucleic acid has been introduced in a medium containing a carbon source, causing generation and accumulation of a polyester copolymer in cultured bacterial cells or a culture product, and collecting the polyester copolymer from the cultured bacterial cells or the culture product.

Preferably, each recombinant microorganism of the present invention is cultured under general culture conditions for the microorganism depending on the recombinant microorganism type, except for the medium composition. In particular, culture of a recombinant microorganism under anaerobic conditions is advantageous in that the LA mole fraction in a copolymer polyester can be increased.

A medium with a specific composition is not particularly required herein. However, it is preferable to use a medium with the limited content of a nitrogen source (other than a carbon source), an inorganic salt, or a different organic nutrient. An example of a medium for culturing a recombinant microorganism obtained by incorporating a nucleic acid into a bacterium of the genus *Ralstonia* or *Pseudomonas* is a medium with the nitrogen source content limited to 0.01% to 0.1%.

Examples of a carbon source include carbohydrates such as glucose, fructose, sucrose, and maltose. In addition, a fat-and-oil-related substance with a carbon number of 4 or higher can be used as a carbon source. Examples of a fat-and-oil-related substance with a carbon number of 4 or higher include: natural fat and oil such as corn oil, soybean oil, safflower oil, sunflower oil, olive oil, coconut oil, palm oil, rapeseed oil, fish oil, whale oil, lard, or beef tallow; fatty acid such as butanoic acid, pentanoic acid, hexanoic acid, octanoic acid, decanoic acid, lauric acid, oleic acid, palmitic acid, linolenic acid, linoleic acid, or myristic acid, or an ester of such fatty acid, and alcohol such as octanol, lauryl alcohol, oleyl alcohol, or palmityl alcohol, or an ester of such alcohol.

Examples of a nitrogen source include peptone, meat extract, yeast extract, and corn steep liquor, in addition to ammonium salts such as ammonia, ammonium chloride, ammonium sulfate, and ammonium phosphate. Examples of an inorganic substance include primary potassium phosphate, secondary potassium phosphate, magnesium phosphate, magnesium sulfate, and sodium chloride.

Preferably, culture is carried out under aerobic conditions via general shake culture or the like at 25° C. to 37° C. within 24 hours or longer after transcriptional expression of proteins (1) to (4) described above. When culture is carried out under anaerobic conditions, the time period for culture is preferably 48 hours or longer. During culture, an antibiotic such as kanamycin, ampicillin, or tetracycline may be added to a medium. If all or some of the DNAs encoding proteins (1) to (4) are ligated under the regulation of an inducible promoter, a factor that induces transcription of the promoter may be added to a medium.

In one preferable embodiment of the present invention, the method for producing a polyester copolymer consisting of 3HB and LA comprises culturing recombinant *Escherichia coli* into which an expression vector containing the nucleic acid encoding *M. elsdenii*-derived pct (SEQ ID NO: 3), the nucleic acid encoding *R. eutropha*-derived β KT (SEQ ID NO: 5), the nucleic acid encoding *R. eutropha*-derived AACoA-R (SEQ ID NO: 7), and the nucleic acid encoding STQK has been introduced. In particular, with the use of a microorganism capable of high lactate accumulation such as the *Escherichia coli* strain Jw2293, Jw0885, or Jw0886 as a host, the LA mole fraction in a polyester copolymer can be further increased. In addition, the LA mole fraction in a polyester copolymer can be further increased by culturing *Escherichia coli* as a host under anaerobic conditions.

According to the method of the present invention, a polyester copolymer consisting of 3HB and LA can be produced from inexpensive blackstrap molasses without the addition of a monomer component (e.g., LA or 3HB) that constitutes a polymer of interest to a medium. This is advantageous in terms of production cost.

In the present invention, a polyester can be collected by a method for collecting a polyester copolymer or PHA from a microorganism that is known to persons skilled in the art. For example, bacterial cells are collected from a culture solution via centrifugation, followed by washing and drying. Then, the dried bacterial cells are suspended in chloroform and heated for extraction of a polyester copolymer of interest in a chloroform fraction. Further, methanol is added to the resulting chloroform solution for precipitation of a polyester. The supernatant is removed via filtration or centrifugation, followed by drying. Thus, the purified polyester copolymer can be obtained.

It is possible to confirm whether the collected polyester is a polyester copolymer consisting of 3HB and LA by a general method such as gas chromatography or a nuclear magnetic resonance method.

Further, the present invention provides a method for producing a polyester copolymer comprising 3HB and LA, which comprises the steps of:
1) culturing a recombinant microorganism having a protein capable of catalyzing a reaction of transferring CoA to propionic acid and/or lactate, a protein capable of catalyzing a reaction of forming acetoacetyl-CoA from two acetyl-CoA molecules, a protein capable of catalyzing a reaction of acetoacetyl-CoA reduction, and a protein capable of catalyzing a reaction of polyhydroxyalkanoate synthesis comprising the following amino acid sequence (a) or (b) in a hydroxyalkanoate other than 3HB or LA and a medium containing a carbon source:

(a) an amino acid sequence derived from the amino acid sequence shown in SEQ ID NO: 2 by substitution of at least one of the amino acids at positions 130, 325, 477, and 481 with different amino acid(s); or (b) an amino acid sequence derived from the protein specified in (a) by additional deletion or substitution of at least one amino acid other than the amino acids at positions 130, 325, 477, and 481 or by insertion of at least one amino acid residue; and 2) collecting the polyester copolymer from the culture product obtained in step (1).

Regarding the above method, a protein capable of catalyzing a reaction of transferring CoA to propionic acid and/or lactate, a protein capable of catalyzing a reaction of forming acetoacetyl-CoA from two acetyl-CoA molecules, a protein capable of catalyzing a reaction of acetoacetyl-CoA reduction, a protein capable of catalyzing a reaction of polyhydroxyalkanoate synthesis comprising the amino acid sequence (a) or (b) above, and a recombinant microorganism capable of expressing the proteins are as described above.

The method for producing a polyester copolymer consisting of 3HB and LA of the present invention is characterized in that a recombinant microorganism having such proteins is cultured in a medium containing a hydroxyalkanoate other than 3HB or LA and a carbon source. A recombinant microorganism produces 3HB and LA by itself. By adding a precursor that can be converted into a polyester copolymer monomer unit other than 3HB or LA to a medium, a polyester copolymer comprising 3HB, LA, and a different monomer unit can be produced.

Examples of such precursor (a monomer unit converted therefrom) include propionic acid (3-hydroxypropionate), valeric acid (3-hydroxyvalerate), dodecanoic acid (3-hydroxyhexanoate, 3-hydroxyoctanoate, 3-hydroxydodecanoate, or 3-hydroxydodecanoate), 4-hydroxybutyrate (4-hydroxybutyrate), and 4-hydroxyvalerate (4-hydroxyvalerate). Any of these examples can be used in the present invention. Such precursor may have been previously added to a medium or may be added to a medium in a time-dependent manner. In addition, the LA mole fraction can be controlled by carrying out culture for producing a polyester copolymer comprising 3HB, LA, and a different monomer unit under anaerobic conditions.

The present invention is described below in more detail with reference to the Examples in a non-limited manner. In addition, experimental operations used in the Examples were conducted according to manuals introducing experimental operations (e.g., Sambrook et al., Molecular cloning: a laboratory manual, 2nd ed. 1989, Cold Spring Harbor Laboratory Press, Cold Spring Harbor, N.Y.) and instructions included with a variety of reagents and kits.

EXAMPLES

Example 1

Production of a Polyester Copolymer with the Use of *Escherichia Coli* Capable of High LA Accumulation (1) Production of a Recombinant Microorganism Genomic DNA was extracted from *M. elsdenii* (ATCC17753) with the use of a DNeasy Tissue Kit (Qiagen). Subsequently, primer DNA of a forward primer comprising the EcoRI recognition sequence and that of a reverse primer comprising the PstI recognition sequence were synthesized in order to amplify a nucleic acid encoding propionyl CoA transferase (accession No. J04987) by PCR. PCR reaction was performed for 1 cycle of 94° C. for 2 minutes and 30 cycles of 94° C. for 15 seconds, 55° C. for 30 seconds, and 68° C. for 2 minutes in a reaction solution containing KOD-Plus-DNA polymerase (1U), PCR buffer, 1 mM MgSO$_4$, the primers (15 pmol each), and 0.2 mM dNTPs (each produced by TOYOBO Co., Ltd.) by means of iCycler (BioRad) with the use of the genomic DNA as a template. Then, an amplified fragment with a size of approximately 1,500 by was collected, followed by digestion with EcoRI and PstI. Thus, a DNA fragment was obtained.

Plasmid pTV118N (Takara Shuzo Co., Ltd.) was digested with EcoRI and PstI, followed by dephosphorylation with alkaline phosphatase. Subsequently, ligation was performed with the addition of the DNA fragment. Thus, a recombinant plasmid PTV118N M.E.-PCT with a size of approximately 4.7 kbp containing DNA encoding propionyl CoA transferase was prepared.

According to the method described by Takase et al. (J. Biochem., 2003, vol. 133, pp. 139-145), a plasmid pGEMC1 (ST/QK)AB containing DNA encoding *R. eutropha*-derived β-ketothiolase (SEQ ID NO: 5), DNA encoding *R. eutropha*-derived acetoacetyl-CoA reductase (SEQ ID NO: 7), and DNA encoding STQK was prepared.

pGEMC1(ST/QK)AB was digested with BamHI to collect a DNA fragment with a size of approximately 6 kbp. T4 polymerase (200 units) was allowed to act at 37° C. for 5 minutes in a 3 mM Tris acetate buffer solution (pH 7.9) containing 66 mM potassium acetate, 10 mM magnesium acetate, 0.5 mM DTT, 0.1 mg/mL BSA, and 0.1 mM dNTP. Thus, a DNA fragment encoding STQK was obtained.

pTV118N M.E.-PCT was digested with PstI. T4 polymerase was allowed to act under the conditions described above, followed by dephosphorylation with alkaline phosphatase. The above DNA fragment encoding phaCm was subjected to ligation. DNA encoding STQK was introduced to the SalI site of pTV118N M.E.-PCT. Thus, plasmid pTV118NPCTC1(ST/QK)AB (approximately 9.6 kbp) (FIG. 1) was obtained. Competent cells of the *Escherichia coli* species (JM109) were transformed using pTV118NPCTC1 (ST/QK)AB.

(2) Polymer Production

An LB medium (100 mL) containing 100 μg/mL ampicillin, 2% glucose, and 10 mM pantothenic acid was inoculated with the obtained transformant, followed by culture at 37° C. for 72 hours. After culture, centrifugation was performed at 4° C. at 3,100 rpm for 15 minutes to collect bacterial cells. The bacterial cells were suspended in a 10 mM Tris hydrochloride buffer solution (pH 7.5) and centrifuged again under the above conditions, followed by lyophilization for 2 days.

The dried bacterial cells were placed in a pressure-proof glass reaction tube. Chloroform (3 mL) was added thereto to result in a suspension. The suspension was retained in a heat block at 100° C. for 3 hours, followed by cooling to room temperature. Then, the suspension was filtrated through a 0.2-μm PTFE filter (ADVANTEC) for separation of the chloroform solution from the bacterial cells. The filtrate was placed in a glass test tube for centrifugation and dried at 60° C. such that chloroform was distilled away. A membranous polymer remaining in the test tube was washed with hexane and dried. Another portion of chloroform (3 mL) was added thereto. Thus, a chloroform solution containing the polymer was obtained. The solution was filtrated through a 0.2-μm PTFE filter (ADVANTEC). The polymer fraction was fractionated by a GPC (gel permeation chromatography) system (LC-9201) for fractionation. Then, chloroform was distilled away. Thus, a polymer (48.62 mg) was collected. The polymer content in bacterial cells (percentage of the total dried bacterial cell weight after culture accounted for by the collected polymer weight) was 16.65%.

(3) Polymer Analysis (i) GPC

Chloroform (1 mL) was added to the polymer (approximately 1 mg) collected in (2) above, followed by filtration with a 0.2-μm PTFE filter (ADVANTEC). The resulting solution was used as a sample and subjected to determination by GPC under the conditions described below.

Figure 2:
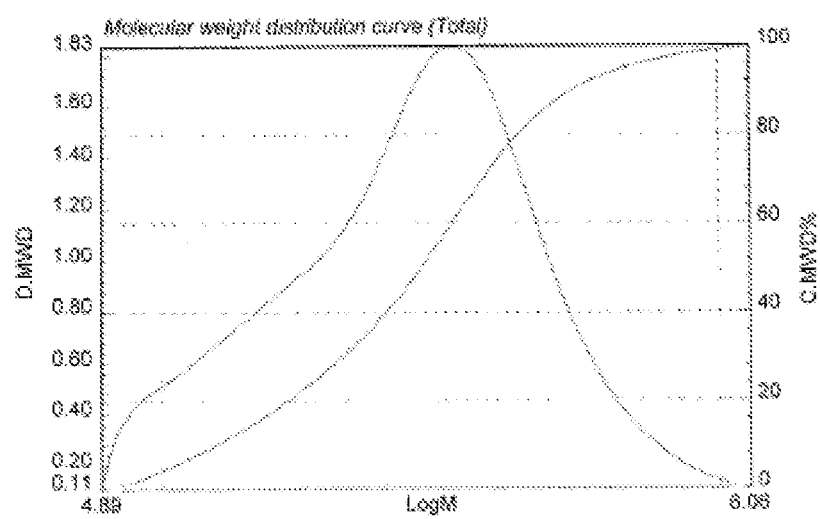
FIG. 2 shows a molecular weight distribution curve for the polymer prepared in Example 1.

System: Shimadzu Prominence GPC system
Column: TSKgel-Super THZ-M (6.0 mm×150 mm)
Eluent: CHCl$_3$
Flow rate: 0.8 mL/minute
Temperature: 40° C.
Detection: 10A refractive index detector
Sample amount: 10 μL FIG. 2 shows a distribution curve of determined molecular weights. A molecular weight calibration curve was created with the use of a standard polystyrene. The molecular weight was represented by a value converted to the standard polystyrene molecular weight. As a result, the polymer molecular weight (mW) was 320,000 and the mean molecular weight (Mn) was 230,000. Accordingly, the Mw/Mn was 1.3.

(ii) Thermal Analysis (DSC)

Figure 3:
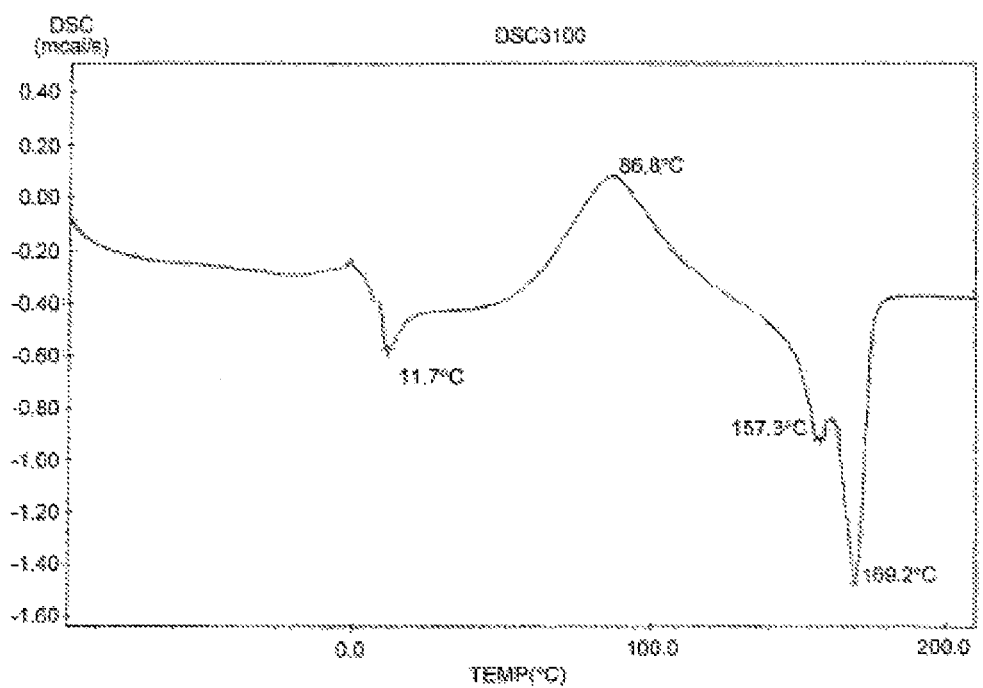
FIG. 3 is a graph showing thermal analysis measurement results for the polymer prepared in Example 1.

The polymer collected in (2) above (approximately 1 mg) was analyzed by a differential scanning calorimeter (DSC3100, Mac Science) under the following conditions: temperature increase from −50° C. to 210° C. (20° C./minute), temperature decrease from 210° C. to −90° C. (40° C./minute), retention at −90° C. for 5 minutes, and temperature increase from −90° C. to 210° C. (20° C./minute) (FIG. 3).

As a result, the glass transition temperature was found to be approximately 0° C., the degree of crystallinity was found to be 86.8° C., and the Tm (melting point) of polymer was found to be 157.3° C. to 157.5° C.

(iii) GC/MS

A solution obtained by dissolving the polymer collected in (2) above (approximately 50 μg) in chloroform (1 mL) (250 μL), ethanol (850 μL), and hydrochloric acid (100 μL) were mixed in a pressure-proof glass reaction tube, followed by ethanolysis treatment in a heat block at 100° C. for 3 hours. The mixture was cooled to room temperature. A solution containing 0.65 M phosphoric acid and 0.9 M NaCl (1 ml) and a 250 mM phosphoric acid solution (500 μL) were added thereto, followed by mixing. Then, the pH was adjusted to neutral. The resultant was centrifuged at room temperature at 1,200 rpm for 5 minutes for separation of the water layer from the chloroform layer. The chloroform layer was collected, followed by dehydration with molecular sieves. Thus, the GC analysis sample was obtained.

GC/MS analysis was carried out under the following conditions.

Figure 4:
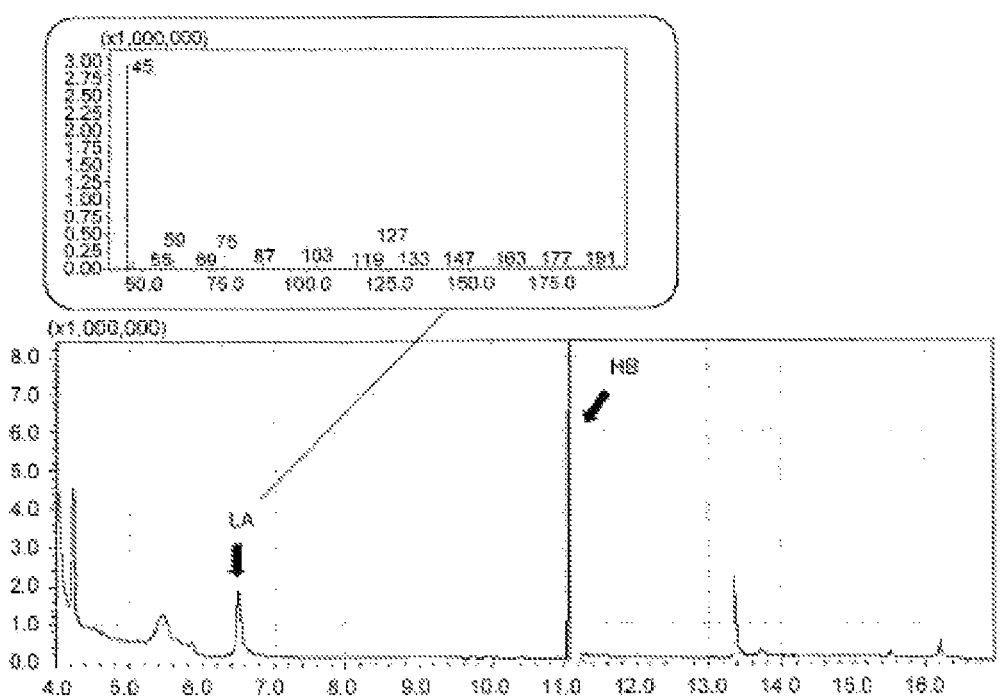
FIG. 4 is a chart showing GC/MA analysis results for the polymer prepared in Example 1.

GC system: Shimadzu GC 2010
MS system: GC/MS-QP2010
Column: NEUTRA-BOND-1 (0.25 mm×3000 mm)
Carrier gas: He
Gas flow rate: 30.0 mL/minute
Detector temperature: 310° C.
Injector temperature: 250° C.
Column oven temperature: 100° C.
Column temperature increase: 8° C./minute
Sample amount: 1 μL FIG. 4 shows analysis results obtained under the above conditions and the MS spectrum for ethyl lactate. As a result of GC/MS, the polymer collected in (2) was confirmed to contain 3HB and LA as monomer units.

(iv) NMR Analysis

Figure 5:
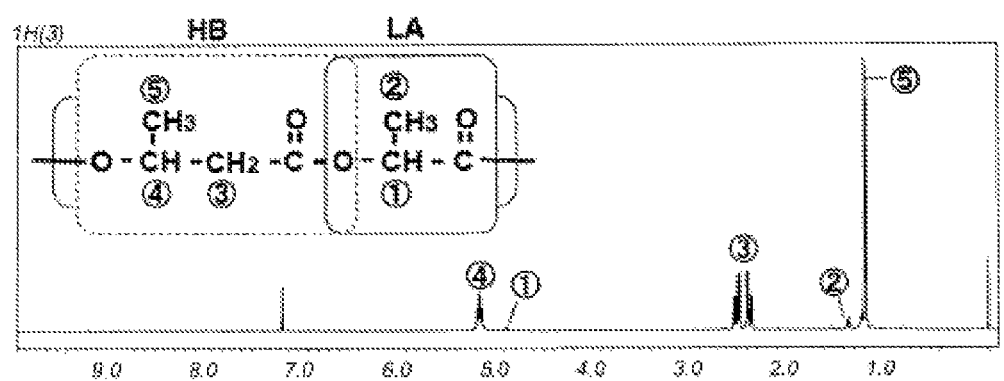
FIG. 5 is a chart showing $^1$H-NMR spectral analysis results for the polymer prepared in Example 1.
Figure 6:
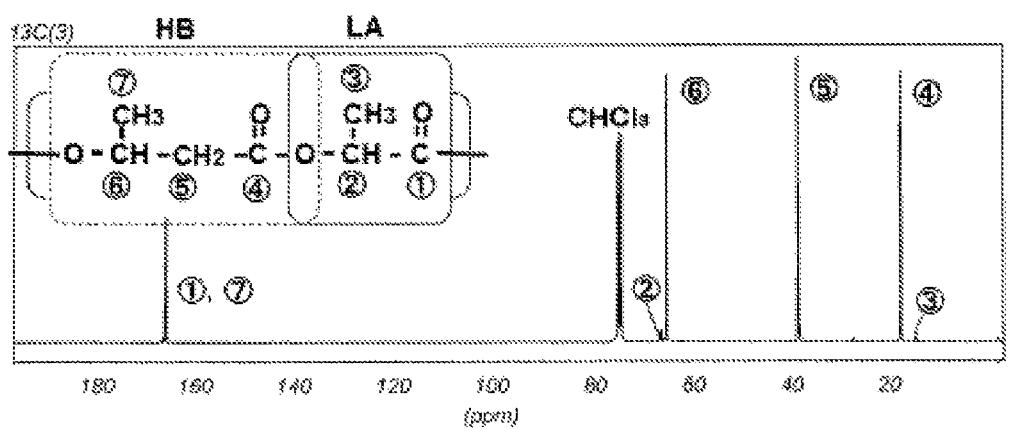
FIG. 6 is a chart showing $^{13}$C-NMR spectral analysis results for the polymer prepared in Example 1.
Figure 7:
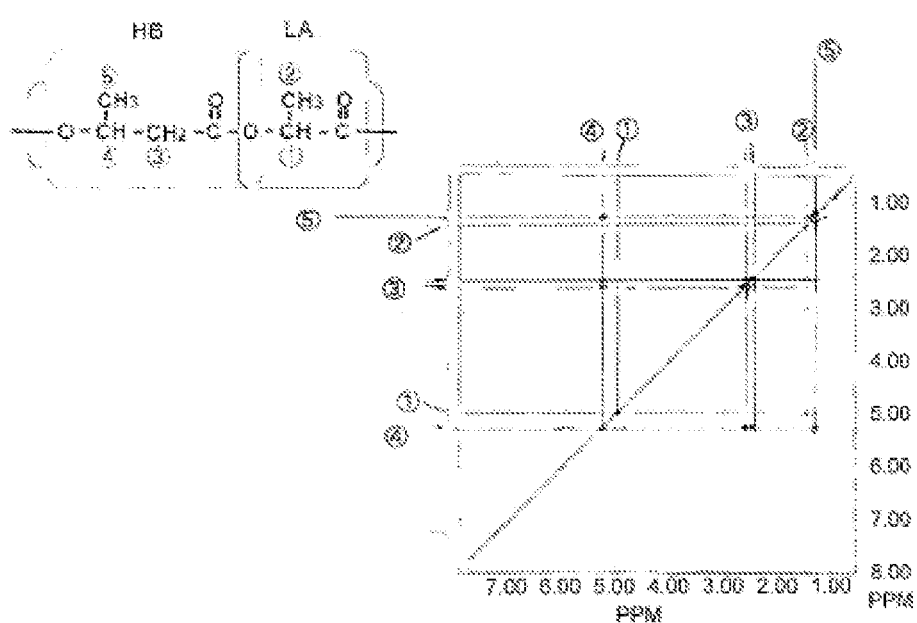
FIG. 7 is a chart showing $^1$H$^1$H-NMR spectral analysis results for the polymer prepared in Example 1.
Figure 8:
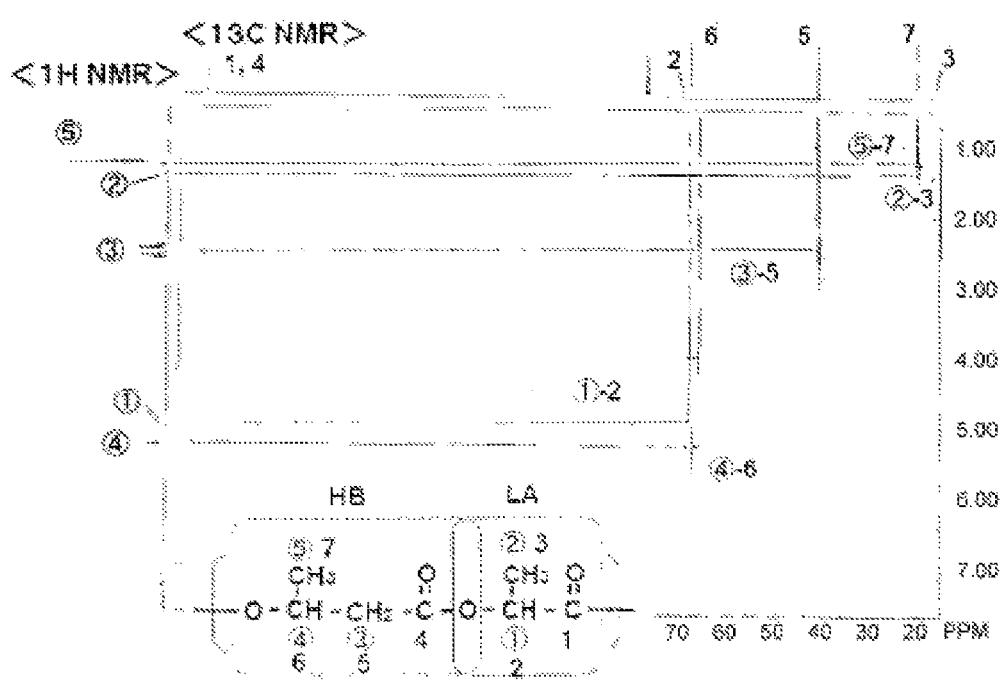
FIG. 8 is a chart showing $^{13}$C$^1$H-NMR spectral analysis results for the polymer prepared in Example 1.

A sample was prepared by dissolving the polymer collected in (2) in deuterated chloroform, followed by $^1$H-NMR (FIG. 5), $^{13}$C-NMR (FIG. 6), $^1$H$^1$H-NMR (FIG. 7), and $^{13}$C$^1$H-NMR (FIG. 8) determination at 300 MHz. As a result, it was found that the polymer collected in (2) contained 3HB and LA as monomer units and the ratio of 3HB to LA was approximately 94:6.

Comparative Example

Figure 9:
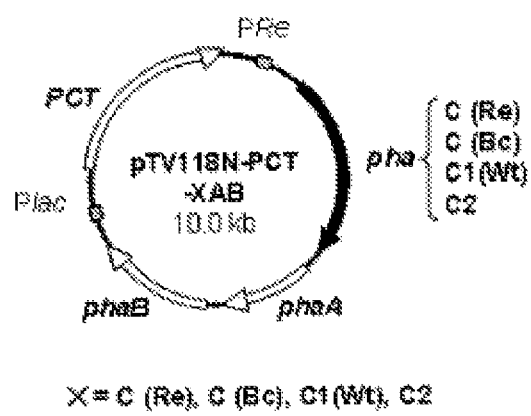
FIG. 9 schematically shows the configuration of a recombinant plasmid pTV118NPCTC(Re)AB, pTV118NPCTC(Bc)AB, pTV118NPCTC1(WT)AB, or pTV118NPCTC2AB.

Expression vectors were prepared by substituting the nucleotide sequence encoding STQK contained in plasmid pTV118NPCTC1(ST/QK)AB prepared in Example 1 with a different one of the nucleotide sequences encoding the proteins described below. The configuration common to all the expression vectors is shown in FIG. 9.

pTV118NPCTC(Re)AB: *R. eutropha*-derived polyhydroxyalkanoate synthase (accession number: J05003)

pTV118NPCTC(Bc)AB: *B. cereus*-derived polyhydroxyalkanoate synthase (accession number: DQ486135)

pTV118NPCTC1(WT)AB: *Pseudomonas* sp. 61-3-derived polyhydroxyalkanoate synthase (wild type: SEQ ID NO: 1)

pTV118NPCTC2AB: *Pseudomonas* sp. 61-3-derived polyhydroxyalkanoate synthase 2 (accession number: AB014758)

Each of the above expression vectors was used for transformation of *Escherichia coli* JM109. An LB medium (100 ml) containing ampicillin (100 µg/ml), 2% glucose, and 10 mM pantothenic acid was inoculated with a different *Escherichia coli* JM109 transformant, followed by culture at 37° C. for 72 hours. Bacterial cells were collected and suspended in 10 mM Tris-HCl (pH 7.5). The cells were again collected and lyophilized for 2 days. The dried bacterial cells were placed in a pressure-proof glass reaction tube. Chloroform (3 mL) was added thereto to result in a suspension. The obtained suspension was retained in a heat block at 100° C. for 3 hours, followed by cooling to room temperature. Then, the suspension was filtrated through a 0.2-µm PTFE filter (ADVANTEC) for separation of the chloroform solution from the bacterial cells. The filtrate was placed in a glass test tube used for centrifugation and dried at 60° C. such that chloroform was distilled away. A membranous polymer remaining in the test tube was washed with hexane and dried. The resultant was dissolved again in chloroform (3 mL). Thus, a chloroform solution containing the polymer was obtained.

The solution was filtrated through a 0.2-µm PTFE filter (ADVANTEC). The polymer fraction was fractionated by GPC (Preparative chromatography: LC-9201) used for fractionation. Chloroform was distilled away. Thus, a polymer was obtained. The amounts of the respective polymers were as follows: pTV118NPCTC(Re)AB: 131.41 mg; pTV118NPCTC(Bc)AB: 160.61 mg; pTV118NPCTC1(WT)AB: Not detected; pTV118NPCTC2AB: Unquantified (infinitesimal amount).

In addition, polymers pTV118NPCTC(Re)AB and pTV118NPCTC(Bc) (50 µg each) and polymer pTV118NPCTC2AB (full amount) were subjected to GC/MS analysis as described in (iii) in (3) of Example 1. Each of the obtained polymers was found to be a homopolymer PHB consisting of 3HB as a monomer unit (FIG. 10).

Example 2

Production of a Microorganism Capable of High LA Accumulation (1) Polymer Production The Jw2293, Jw0885, and Jw0886 strains of *Escherichia coli* capable of high LA accumulation were transformed with the use of pTV118NPCTC1(ST/QK)AB1 prepared in (1) of Example 1.

An LB medium (1000 mL) containing 100 µg/mL ampicillin, 2% glucose, and 10 mM pantothenic acid was inoculated with a different one of the obtained transformants, followed by culture at 37° C. for 72 hours. After culture, centrifugation was performed at 4° C. at 3,100 rpm for 15 minutes to collect bacterial cells. The bacterial cells were suspended in a 10 mM Tris hydrochloride buffer solution (pH 7.5) and centrifuged again under the above conditions, followed by lyophilization for 2 days.

The dried bacterial cells were placed in a pressure-proof glass reaction tube. Chloroform (40 mL) was added thereto to result in a suspension. The suspension was retained in a heat block at 100° C. for 3 hours, followed by cooling to room temperature. Then, the suspension was filtrated through a 0.2-µm PTFE filter (ADVANTEC) for separation of the chloroform solution from the bacterial cells. The filtrate was placed in a glass test tube for centrifugation and dried at 60° C. such that chloroform was distilled away. A membranous polymer remaining in the test tube was washed with hexane and dried. The resultant was dissolved again in chloroform (40 mL). Thus, a chloroform solution was obtained. The solution was filtrated through a 0.2-µm PTFE filter (ADVANTEC). The polymer fraction was fractionated by a GPC system (LC-9201) for fractionation. Then, chloroform was distilled away. Thus, a polymer was obtained.

The amounts of the collected polymers were 802 mg (Jw2293), 804 mg (Jw0885), and 806 mg (Jw0886). In addition, the polymer contents in bacterial cells (percentages of the dried bacterial cell weight after culture accounted for by the collected polymer weight) were 41% (Jw2293), 50% (Jw0885), and 54% (Jw0886).

(2) Polymer Analysis
(i) GPC

Chloroform (1 mL) was added to the polymer (approximately 1 mg) collected in (1) above, followed by filtration with a 0.2-µm PTFE filter (ADVANTEC). The resulting solution was used as a sample and subjected to determination by GPC under the conditions described below.

Figure 11A:
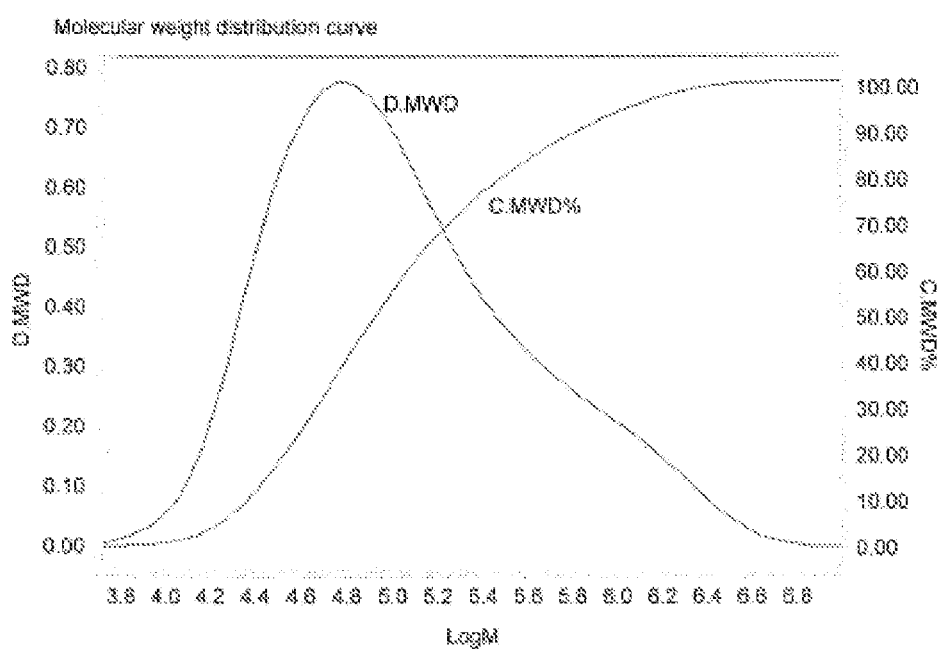
FIG. 11*a* shows a molecular weight distribution curve for the polymer from the *Escherichia coli* Jw2293 strain capable of high LA accumulation prepared in Example 2.
Figure 11B:
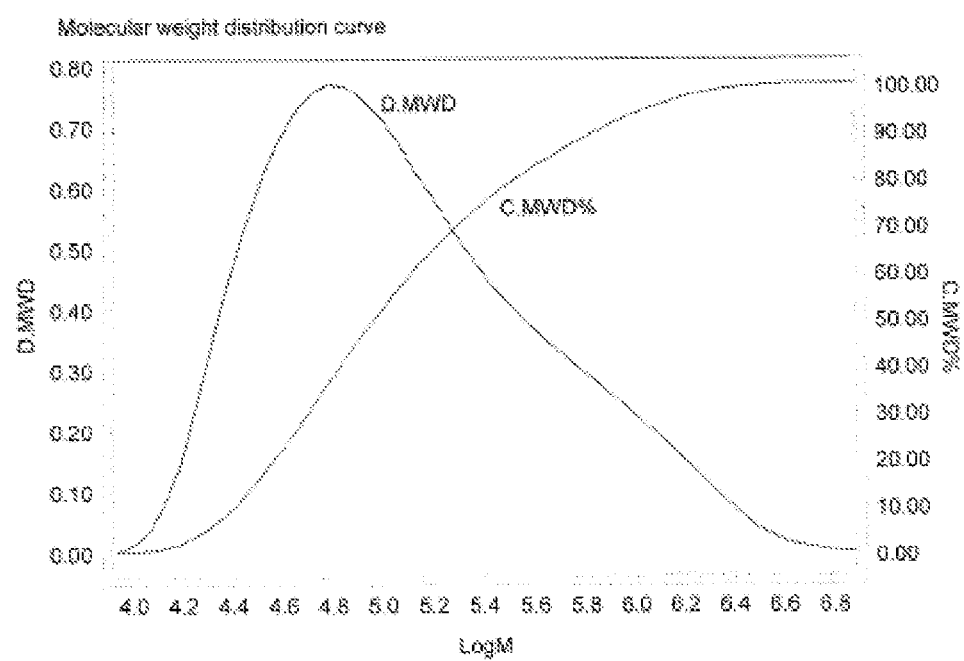
FIG. 11*b* shows a molecular weight distribution curve for the polymer from the *Escherichia coli* Jw0885 strain capable of high LA accumulation prepared in Example 2.
Figure 11C:
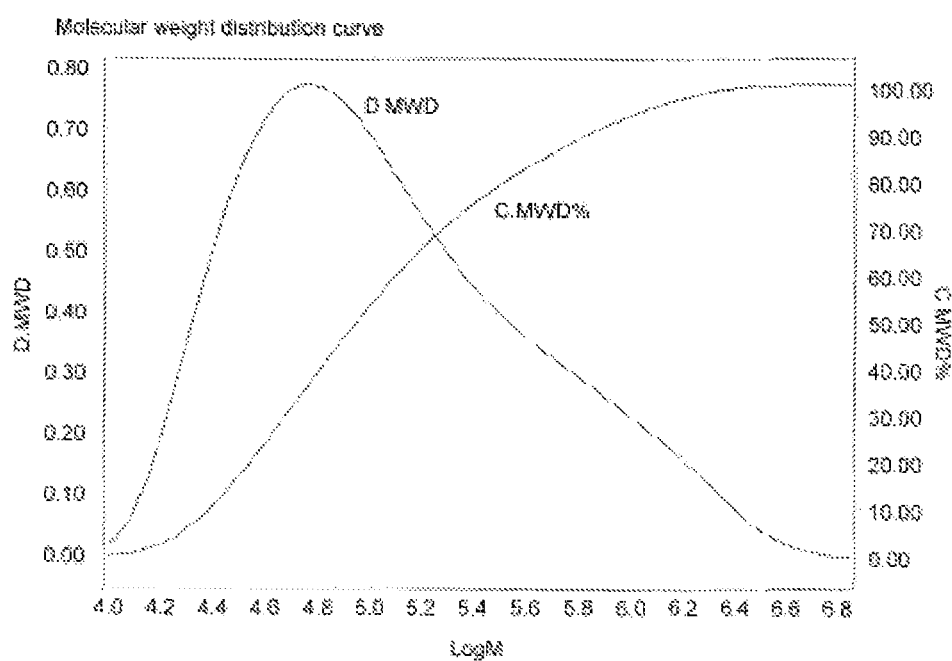
FIG. 11*c* shows a molecular weight distribution curve for the polymer from the *Escherichia coli* Jw0886 strain capable of high LA accumulation prepared in Example 2.

System: PU-2080 Plus system (JASCO)
Column: GPC K-806L (8.0 mm inner diameter×300 mm) (Shodex)
Eluent: $CHCl_3$
Flow rate: 0.8 mL/minute
Temperature: 40° C.
Detection: 10A refractive index detector (JASCO)
Injection amount: 10 µL Each of FIGS. 11a to 11c shows a distribution curve of determined molecular weights. A molecular weight calibration curve was created with the use of a standard polystyrene. The molecular weight was represented by a value converted to the standard polystyrene molecular weight. As a result, the polymer molecular weights (mW) were as follows: the Jw2293 strain-derived polymer: Mw=280,000, Mn=58,000; the Jw0885 strain-derived polymer: Mw=280,000, Mn=66,000; and the Jw0886 strain-derived polymer: Mw=280,000, Mn=64,000. In addition, the Mw/Mn was 4 for each polymer.

(ii) Thermal Analysis (DSC)

Figure 12C:
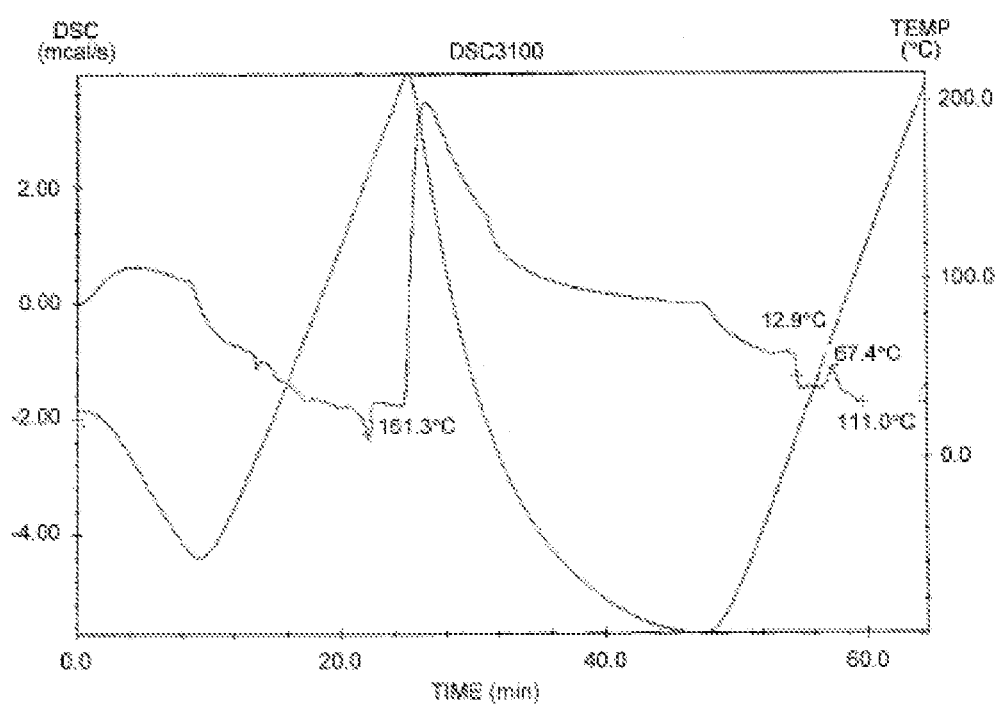
FIG. 12*c* is a graph showing thermal analysis measurement results for the polymer from the *Escherichia coli* Jw0886 strain capable of high LA accumulation prepared in Example 2.

The polymer collected in (2) above (approximately 1 mg) was analyzed by a differential scanning calorimeter (DSC3100, Mac Science) under the following conditions: temperature increase from −50° C. to 210° C. (20° C./minute), temperature decrease from 210° C. to −90° C. (40° C./minute), retention at −90° C. for 5 minutes, and temperature increase from −90° C. to 210° C. (20° C./minute) (FIGS. 12a to 12c).

As a result, the Tm of polymer was found to be 111° C. to 163° C.

(iii) GC/MS

A solution obtained by dissolving the polymer collected in (2) above (approximately 50 µg) in chloroform (1 mL) (250 µL), ethanol (850 µL), and hydrochloric acid (100 µL) were mixed in a pressure-proof glass reaction tube, followed by ethanolysis treatment in a heat block at 100° C. for 3 hours. The mixture was cooled to room temperature. A solution containing 0.65 M phosphoric acid and 0.9 M NaCl (1 ml) and a 250 mM phosphoric acid solution (500 μL) were added thereto, followed by mixing. Then, the pH was adjusted to neutral. The resultant was centrifuged at room temperature at 1,200 rpm for 5 minutes for separation of the water layer from the chloroform layer. The chloroform layer was collected, followed by dehydration with molecular sieves. Thus, the GC analysis sample was obtained.

Figure 13B:
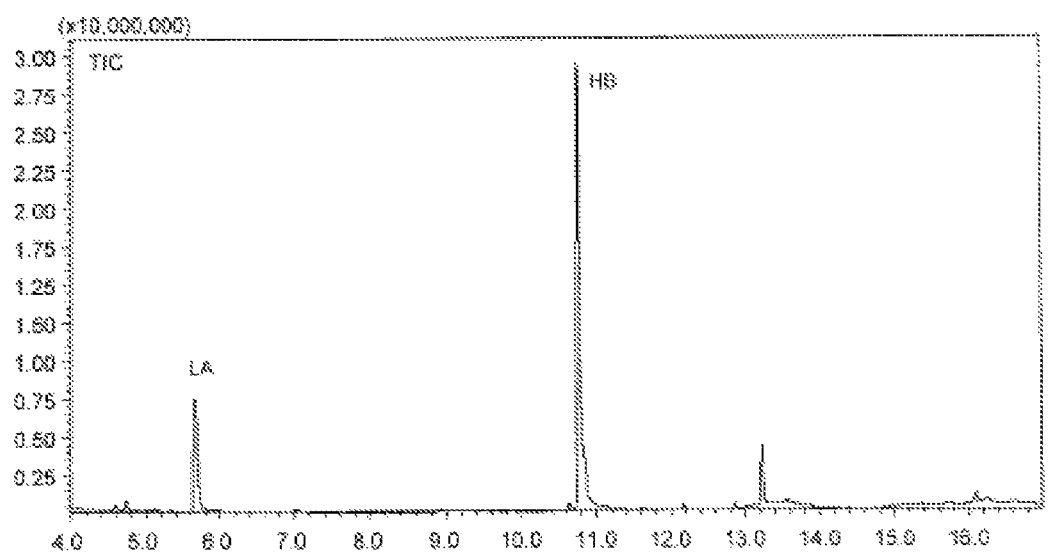
FIG. 13*b* is a chart showing GC/MS analysis results for the polymer from the *Escherichia coli* Jw0885 strain capable of high LA accumulation prepared in Example 2.

GC/MS analysis was carried out under the following conditions.
GC system: Shimadzu GC 2010
MS system: GC/MS-QP2010
Column: NEUTRA-BOND-1 (0.25 mm×3000 mm)
Carrier gas: He
Gas flow rate: 30.0 mL/minute
Detector temperature: 310° C.
Injector temperature: 250° C.
Column oven temperature: 100° C.
Column temperature increase: 8° C./minute
Sample amount: 1 μL Each of FIGS. 13a to 13c shows analysis results obtained under the above conditions and the MS spectrum for ethyl lactate. As a result of GC/MS, the polymer collected in (2) was confirmed to contain 3HB and LA as monomer units.

(iv) NMR Analysis

Figure 14A:
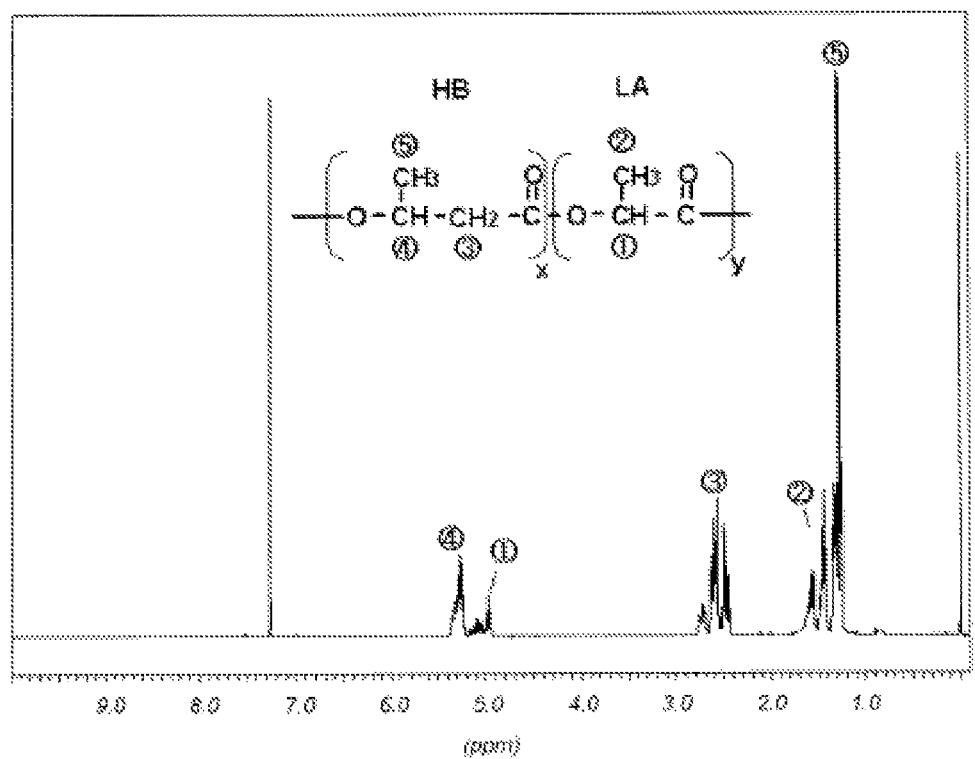
FIG. 14*a* is a chart showing $^1$H-NMR spectral analysis results for the polymer from the *Escherichia coli* Jw2293 strain capable of high LA accumulation prepared in Example 2.
Figure 14B:
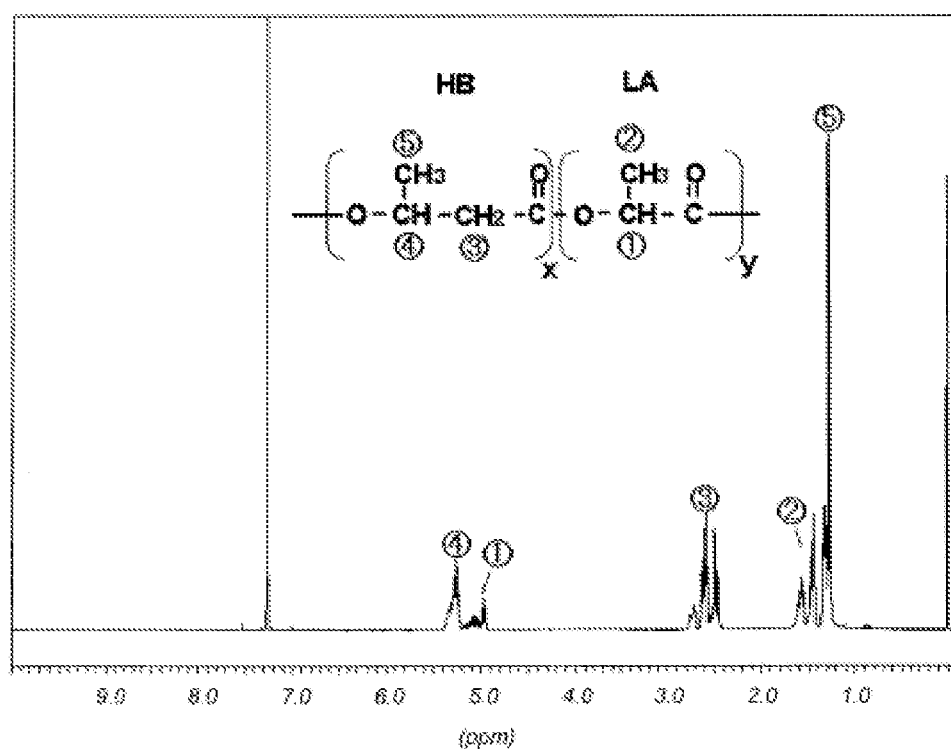
FIG. 14*b* is a chart showing $^1$H-NMR spectral analysis results for the polymer from the *Escherichia coli* Jw0885 strain capable of high LA accumulation prepared in Example 2.
Figure 14C:
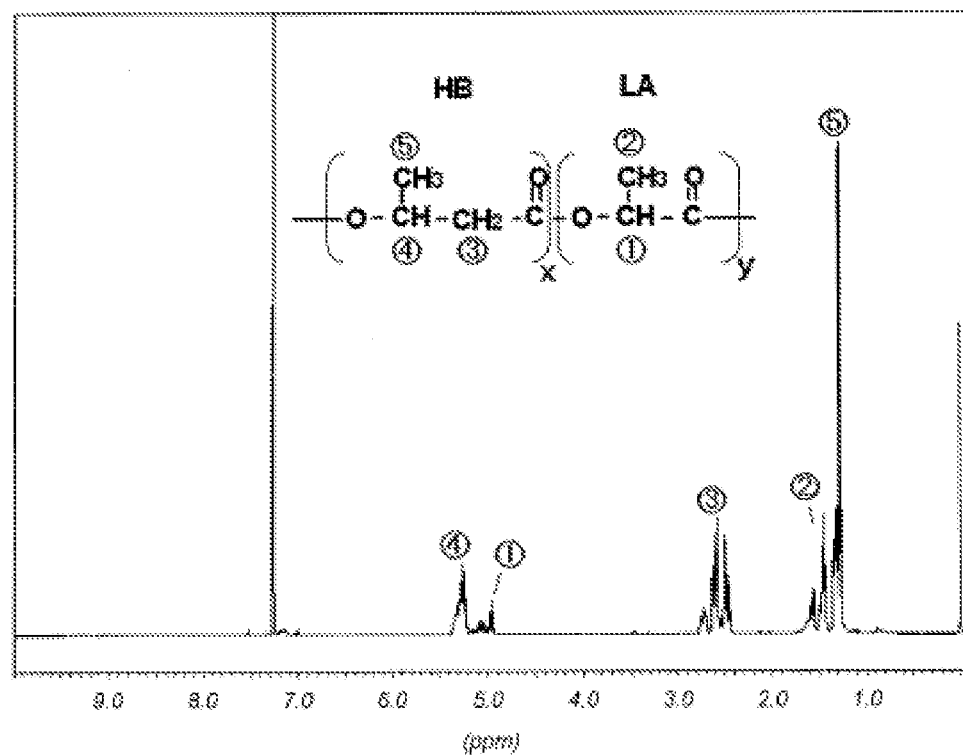
FIG. 14*c* is a chart showing $^1$H-NMR spectral analysis results for the polymer from the *Escherichia coli* Jw0886 strain capable of high LA accumulation prepared in Example 2.
Figure 15A:
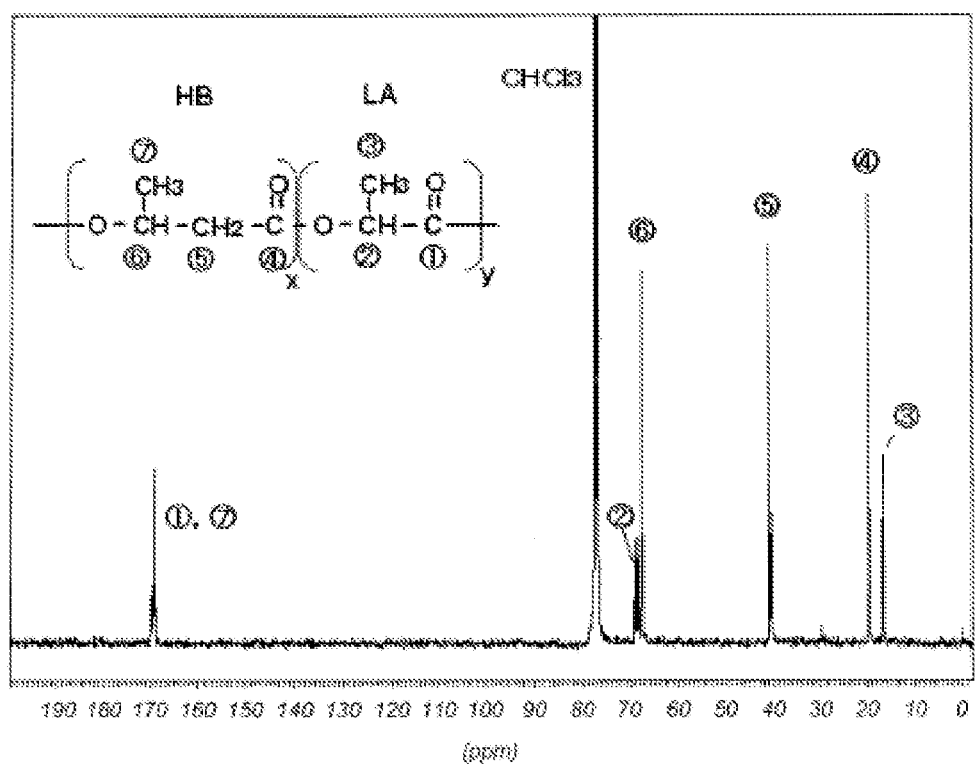
FIG. 15*a* is a chart showing $^{13}$C-NMR spectral analysis results for the polymer from the *Escherichia coli* Jw2293 strain capable of high LA accumulation prepared in Example 2.
Figure 15B:
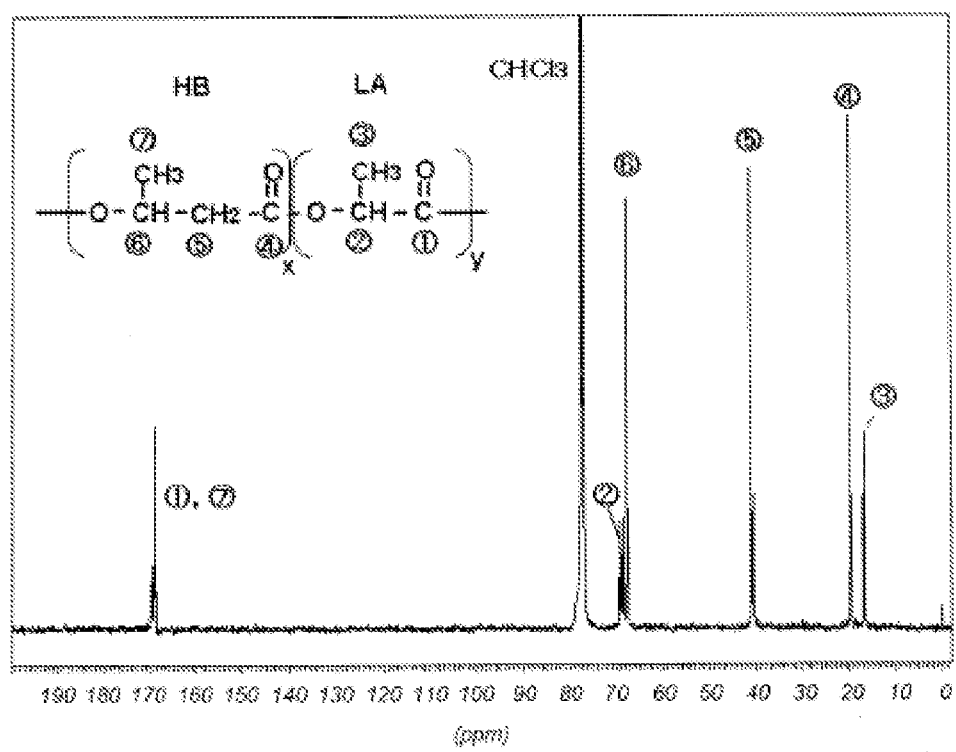
FIG. 15*b* is a chart showing $^{13}$C-NMR spectral analysis results for the polymer from the *Escherichia coli* Jw0886 strain capable of high LA accumulation prepared in Example 2.
Figure 15C:
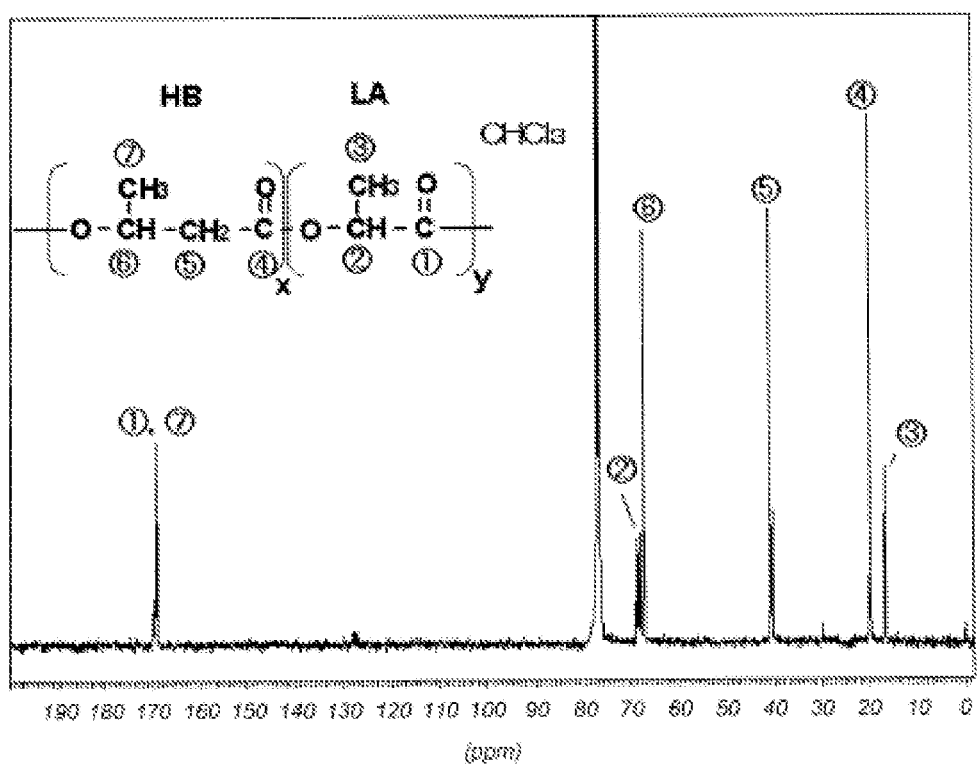
FIG. 15*c* is a chart showing $^{13}$C-NMR spectral analysis results for the polymer from the *Escherichia coli* Jw0886 strain capable of high LA accumulation prepared in Example 2.

A sample was prepared by dissolving the polymer collected in (2) in deuterated chloroform, followed by $^1$H-NMR (FIGS. 14a to 14c) and $^{13}$C-NMR (FIGS. 15a to 15c) determination at 300 MHz. As a result, it was found that the polymer collected in (2) contained 3HB and LA as monomer units and that the ratio of 3HB to LA was as follows: approximately 32:68 (Jw2293); approximately 30:70 (Jw0885); and approximately 32:68 (Jw0886).

Example 3

Figure 16:
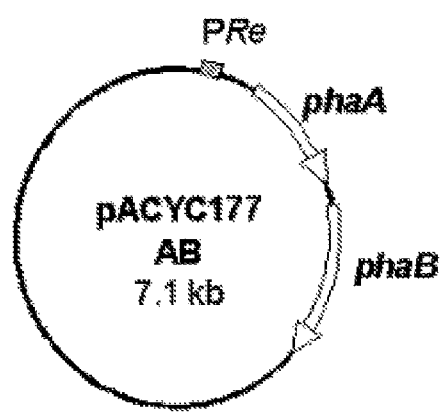
FIG. 16 schematically shows the configuration of a recombinant plasmid pACYC117AB.

Production of a Polyester Copolymer by Culture Under Anaerobic Conditions (1) Vector Construction PCR was performed using pTV118NPCTC1(ST/QK)AB prepared in (1) of Example 1 as a template in a manner allowing linear plasmid lacking the gene encoding β KT and the gene encoding AACoA-R to be obtained. Ring closure was carried out for the obtained amplified fragment. Thus, plasmid pTV118NpctC1(ST/QK) comprising pTV118N having the gene encoding pct and the gene encoding PhaCm (FIG. 16, left) was prepared.

A DNA fragment having approximately 3,200 base pairs obtained by digesting pGEMC1AB prepared in (1) of Example 1 with BamHI (restriction enzyme) was ligated to a linear vector plasmid obtained by digesting a low-copy plasmid pACYC177DNA with BamHI (restriction enzyme). The gene encoding β KT and the gene encoding AACoA-R were introduced into the BamHI site of pACYC177DNA. Thus, plasmid pACYC177AB was obtained (shown in FIG. 16, right).

(2) Polymer Production

The *Escherichia coli* W3110 strain was transformed with the use of pTV118NPCTC1(ST/QK) and pACYC177AB.

An LB medium (100 mL) containing 100 μg/mL ampicillin, 2% glucose, and 10 mM pantothenic acid was inoculated with the obtained transformant, followed by culture at 37° C. for 72 hours. After culture, centrifugation was performed at 4° C. at 3,100 rpm for 15 minutes to collect bacterial cells. The bacterial cells were suspended in a 10 mM Tris hydrochloride buffer solution (pH 7.5) and centrifuged again under the above conditions, followed by lyophilization for 2 days.

The dried bacterial cells were placed in a pressure-proof glass reaction tube. Chloroform (60 mL) was added thereto to result in a suspension. The suspension was retained in a heat block at 100° C. for 3 hours, followed by cooling to room temperature. Then, the suspension was filtrated through a 0.2-μm PTFE filter (ADVANTEC) for separation of the chloroform solution from the bacterial cells. The filtrate was placed in a glass test tube for centrifugation and dried at 60° C. such that chloroform was distilled away. A membranous polymer remaining in the test tube was washed with hexane and dried. The resultant was dissolved again in chloroform (60 mL). Thus, a chloroform solution was obtained. The solution was filtrated through a 0.2-μm PTFE filter (ADVANTEC). The polymer fraction was fractionated by a GPC system (LC-9201) for fractionation. Then, chloroform was distilled away. Thus, a polymer was obtained.

The amount of the collected polymer was 1228 mg. In addition, the polymer content in bacterial cells (percentage of the dried bacterial cell weight after culture accounted for by collected polymer weight) was 2.3%.

(3) Polymer Analysis (i) GPC

Figure 17:
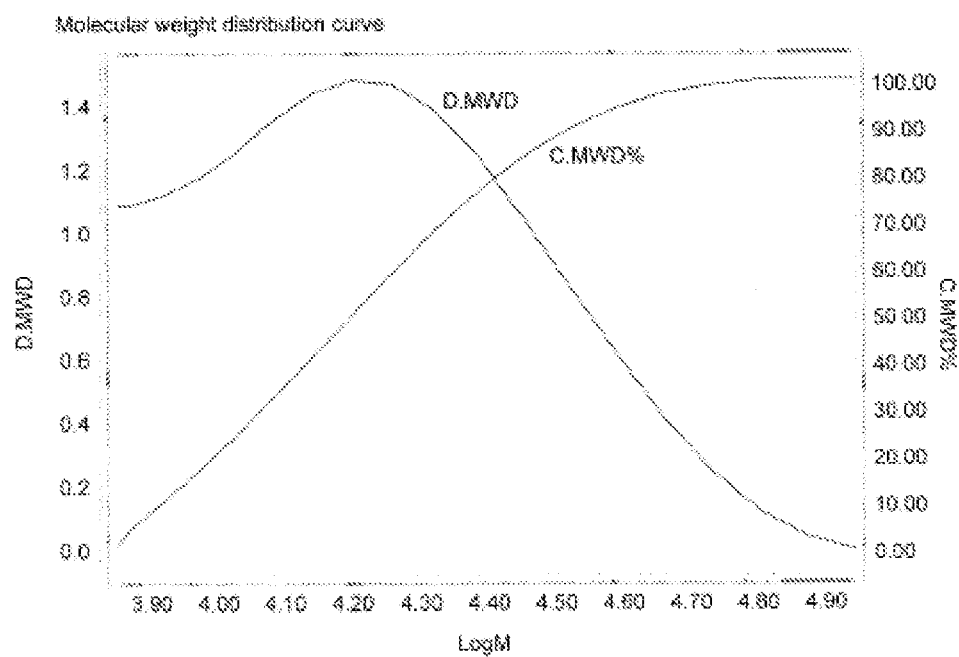
FIG. 17 shows a molecular weight distribution curve for the polymer prepared in Example 3.

Chloroform (1 mL) was added to the polymer (approximately 1 mg) collected in (2) above, followed by filtration with a 0.2-μm PTFE filter (ADVANTEC). The resulting solution was used as a sample and subjected to determination by GPC under the conditions described below.
System: PU-2080 Plus system (JASCO)
Column: GPC K-806L (8.0 mm inner diameter×300 mm) (Shodex)
Eluent: CHCl$_3$
Flow rate: 0.8 mL/minute
Temperature: 40° C.
Detection: 10A refractive index detector (JASCO)
Injection amount: 10 μL FIG. 17 shows a distribution curve of determined molecular weights. A molecular weight calibration curve was created with the use of a standard polystyrene. The molecular weight was represented by a value converted to the standard polystyrene molecular weight. As a result, the polymer molecular weight (mW) was 28,000 and the Mn was 22,000. Accordingly, the Mw/Mn was 1.5.

(ii) Thermal Analysis (DSC)

Figure 18:
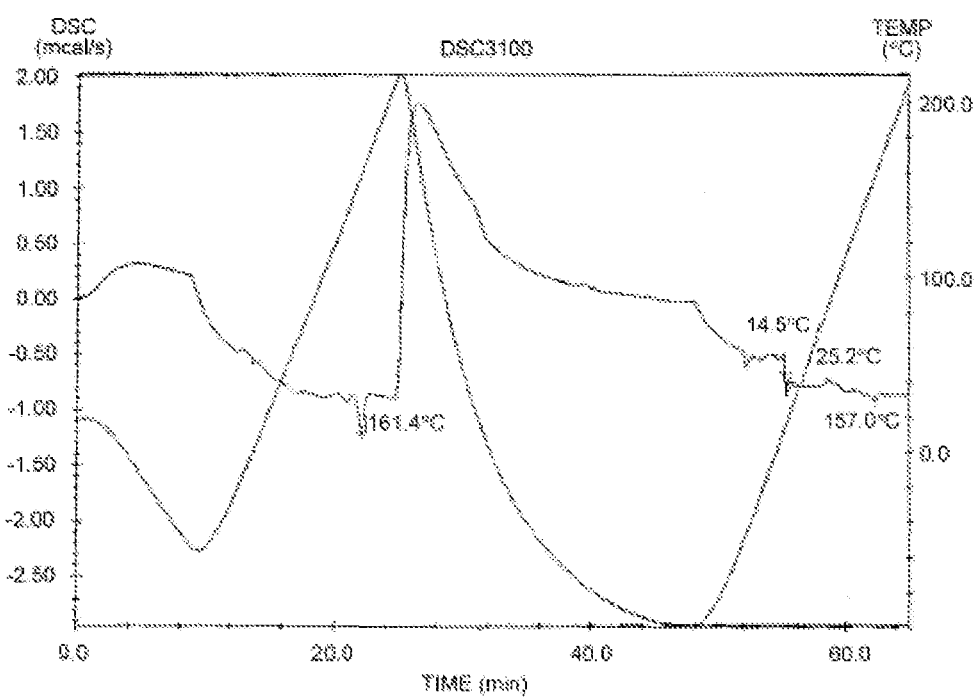
FIG. 18 is a graph showing thermal analysis measurement results for the polymer prepared in Example 3.

The polymer collected in (2) above (approximately 1 mg) was analyzed by a differential scanning calorimeter (DSC3100, Mac Science) under the following conditions: temperature increase from −50° C. to 210° C. (20° C./minute), temperature decrease from 210° C. to −90° C. (40° C./minute), retention at −90° C. for 5 minutes, and temperature increase from −90° C. to 210° C. (20° C./minute) (FIG. 18).

As a result, the Tm (melting point) of polymer was found to be 157.0° C. to 161.4° C.

(iii) GC/MS

A solution obtained by dissolving the polymer collected in (2) above (approximately 50 μg) in chloroform (1 mL) (250 μL), ethanol (850 μL), and hydrochloric acid (100 μL) were mixed in a pressure-proof glass reaction tube, followed by ethanolysis treatment in a heat block at 100° C. for 3 hours. The mixture was cooled to room temperature. A solution containing 0.65 M phosphoric acid and 0.9 M NaCl (1 ml) and a 250 mM phosphoric acid solution (500 μL) were added thereto, followed by mixing. Then, the pH was adjusted to neutral. The resultant was centrifuged at room temperature at 1,200 rpm for 5 minutes for separation of the water layer from the chloroform layer. The chloroform layer was collected, followed by dehydration with molecular sieves. Thus, the GC analysis sample was obtained.

GC/MS analysis was carried out under the following conditions.

Figure 19:
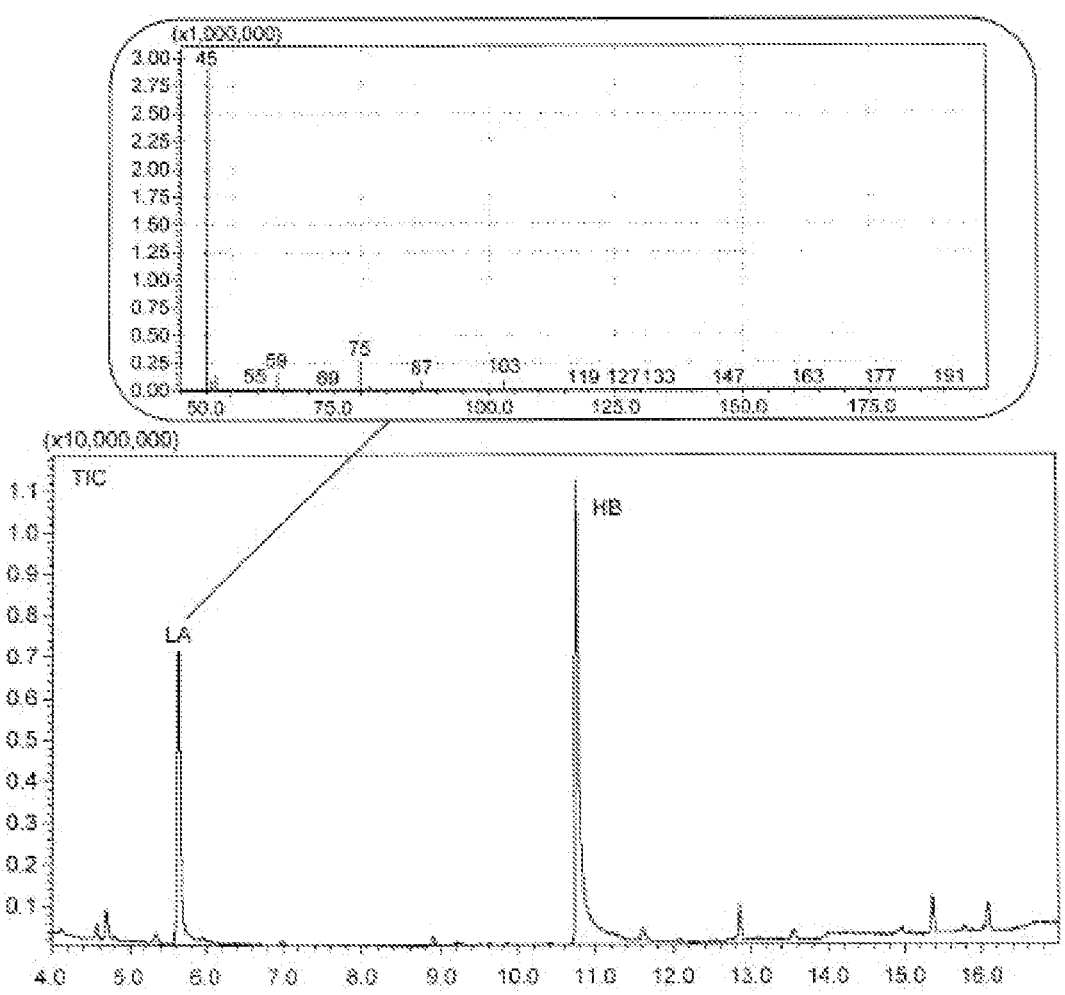
FIG. 19 is a chart showing GC/MS analysis results for the polymer prepared in Example 3.

GC system: Shimadzu GC 2010
MS system: GC/MS-QP2010
Column: NEUTRA-BOND-1 (0.25 mm×3000 mm)
Carrier gas: He
Gas flow rate: 30.0 mL/minute
Detector temperature: 310° C.
Injector temperature: 250° C.
Column oven temperature: 100° C.
Column temperature increase: 8° C./minute
Sample amount: 1 µL FIG. 19 shows analysis results obtained under the above conditions and the MS spectrum for ethyl lactate. As a result of GC/MS, the polymer collected in (2) was confirmed to contain 3HB and LA as monomer units.

(iv) NMR Analysis

Figure 20:
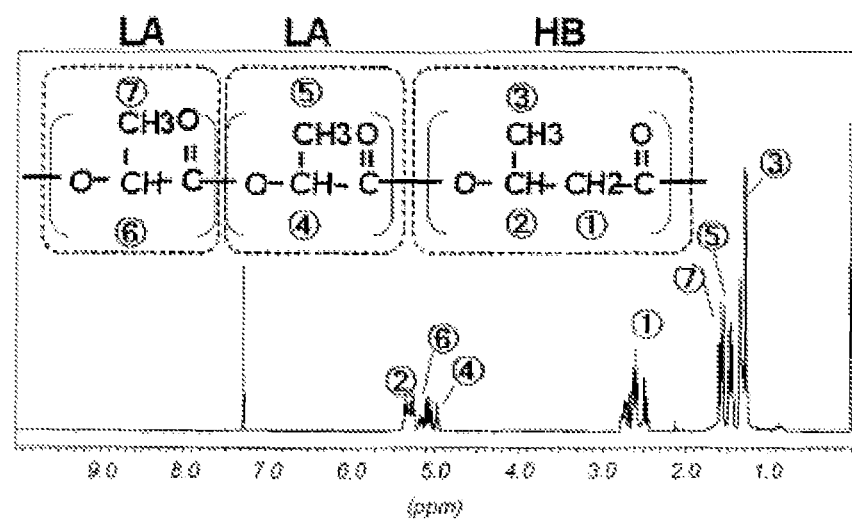
FIG. 20 is a chart showing $^1$H-NMR spectral analysis results for the polymer prepared in Example 3.
Figure 21:
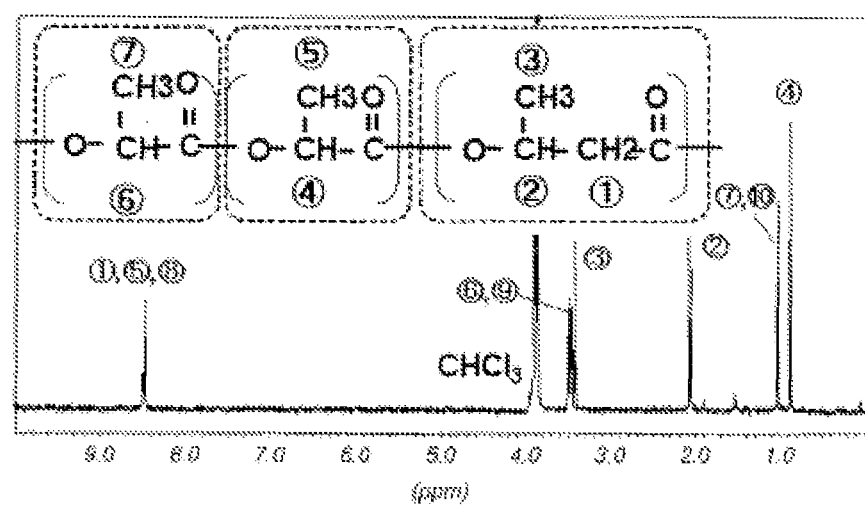
FIG. 21 is a chart showing $^{13}$C-NMR spectral analysis results for the polymer prepared in Example 3.
Figure 2:
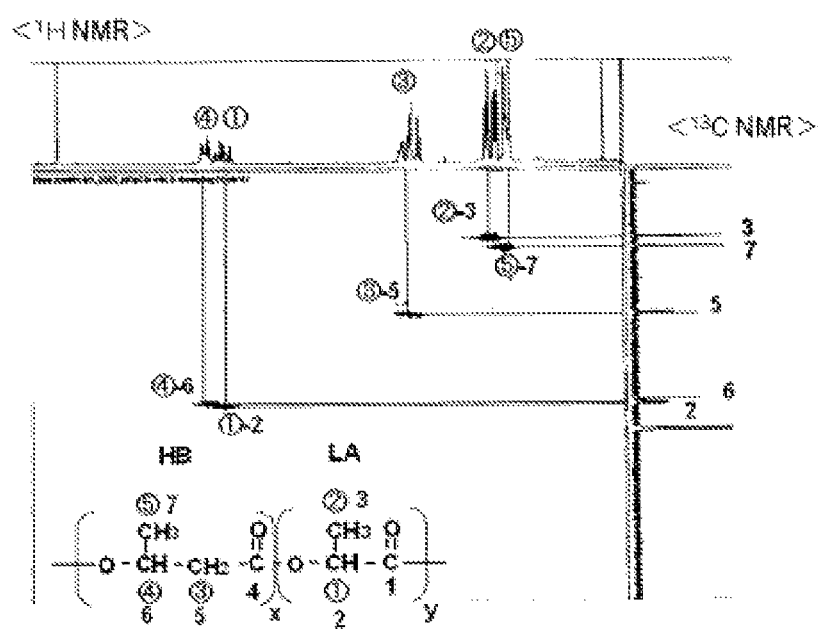

A sample was prepared by dissolving the polymer collected in (2) in deuterated chloroform, followed by $^1$H-NMR (FIG. 20), $^{13}$C-NMR (FIG. 21), and $^{13}$C$^1$H-NMR (FIG. 22) determination at 300 MHz. As a result, it was found that the polymer collected in (2) contained 3HB and LA as monomer units and the ratio of 3HB to LA was approximately 53:47.

Example 4

Production of a Polyester Copolymer Containing 3HB, LA, and 3HV as Monomer Units (1) Polymer Production The *Escherichia coli* strain Jw0885 capable of high lactate accumulation was transformed using pTV118NPCTC1(ST/QK)AB prepared in Example 1. An LB medium (100 mL) containing 100 µg/mL ampicillin, 2% glucose, 10 mM pantothenic acid, and 0.5% sodium propionate (shown in table 1) was inoculated with the obtained transformant, followed by culture at 30° C. for 72 hours. Centrifugation was performed at 4° C. at 3,100 rpm for 15 minutes to collect bacterial cells from the culture product. The bacterial cells were suspended in a 10 mM Tris hydrochloride buffer solution (pH 7.5) and centrifuged again under the above conditions, followed by lyophilization for 2 days.

The dried bacterial cells were placed in a pressure-proof glass reaction tube. Chloroform (5 mL) was added thereto to result in a suspension. The suspension was retained in a heat block at 60° C. for 48 hours, followed by cooling to room temperature. Then, the suspension was filtrated through a 0.2-µm PTFE filter (ADVANTEC) for separation of the chloroform solution from the bacterial cells. Next, methanol (100 ml) was added to the filtrate for polymer precipitation. The precipitate was filtrated through a 0.2-µm PTFE filter (ADVANTEC). Thus, a polymer was obtained.

The amount of the collected polymer was 12 mg. In addition, the polymer content in bacterial cells (percentage of the dried bacterial cell weight after culture accounted for by the collected polymer weight) was 8.5%.

(2) Polymer Analysis (i) HPLC Analysis 1N sodium hydroxide (500 µl) was added to the collected polymer (approximately 10 mg), followed by heating at 100° C. for 3 hours for hydrolysis. After the reaction, the resultant was neutralized with the addition of 1N hydrochloric acid (500 µl) and filtrated through a 0.2-µm PTFE filter (ADVANTEC). The filtrate was designated as a test solution and then subjected to HPLC analysis under the following conditions.

System: PU-2089 Plus system (JASCO)
Column: Aminex HPX-87H (7.8 mm inner diameter×300 mm) (Shodex)
Eluent: 0.014 N sulfuric acid-20% acetonitrile
Flow rate: 0.5 mL/minute
Temperature: 60° C.
Detection: AS-2055 (JASCO)
Injection amount: 10 µL A calibration curve was created using the following polymers with known monomer compositions: polylactate (LA: 100 mol %) and poly[hydroxybutyrate (HB)-co-hydroxyvalerate (HV)-co-hydroxy hexanoate (HHx)](HB: 70 mol %, HV: 23 mol %, HHx: 7 mol %).

Figure 23:
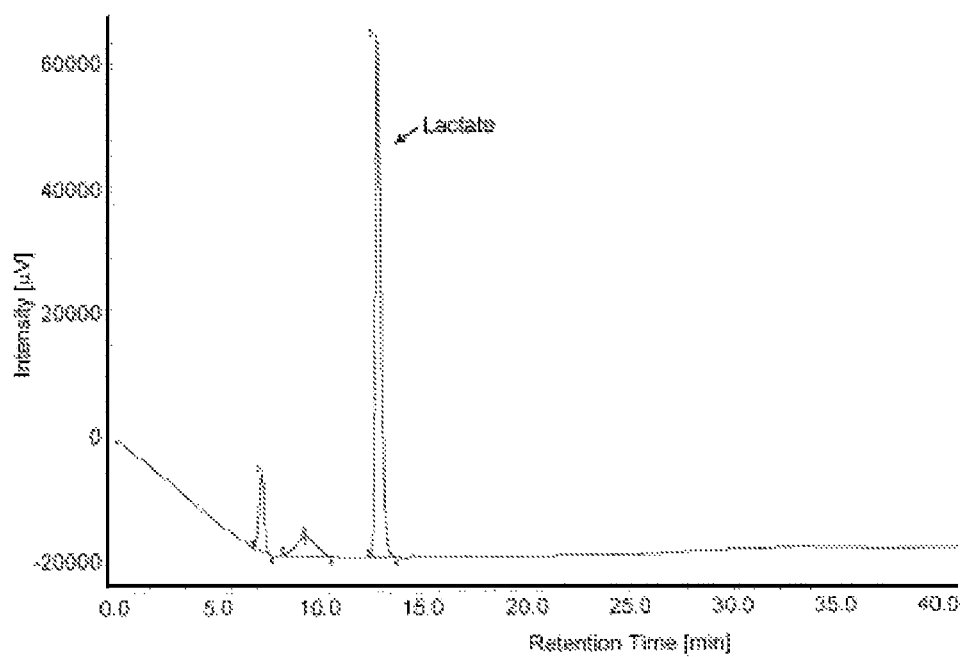
FIG. 23 is an HPLC chart for polylactate used as a standard substance.
Figure 24:
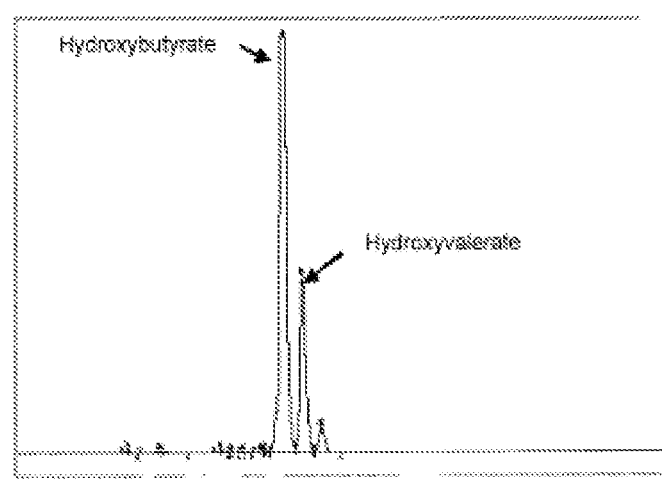
FIG. 24 is an HPLC chart for poly[hydroxybutyrate (HB)-co-hydroxyvalerate (HV)-co-hydroxyhexanoate (HHx)] (HB: 70 mol %; HV: 23 mol %; HHx: 7 mol %) used as a standard substance.
Figure 2:
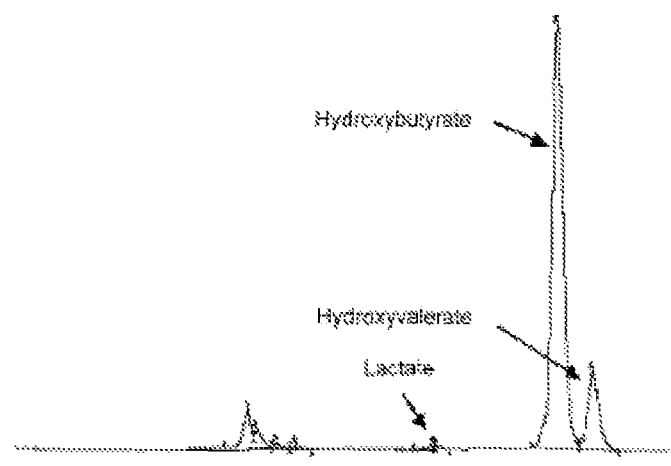

Based on the results (shown in FIGS. 23 to 25), the obtained polymer was confirmed to consist of lactate (approximately 40 mol %), 3-hydroxybutyrate (approximately 48 mol %), and 3-hydroxyvalerate (approximately 11 mol %).

All publications, patents, and patent applications cited herein are incorporated herein by reference in their entirety.

The invention claimed is:

1. A recombinant microorganism that comprises
a protein capable of catalyzing a reaction of transferring CoA to propionic acid and/or lactate, wherein the protein comprises the amino acid sequence of SEQ ID NO: 4;
a protein capable of catalyzing a reaction of forming acetoacetyl-CoA from two acetyl-CoA molecules, wherein the protein comprises the amino acid sequence of SEQ ID NO: 6;
a protein capable of catalyzing a reaction of acetoacetyl-CoA reduction, wherein the protein comprises the amino acid sequence of SEQ ID NO: 8; and
a protein capable of catalyzing a reaction of polyhydroxyalkanoate synthesis, wherein the protein comprises the amino acid sequence of SEQ ID NO: 2 in which Ser at position 325 is substituted with Thr, and Gln at position 481 is substituted with Lys.

2. The recombinant microorganism according to claim 1, wherein any one of said proteins is encoded by a polynucleotide expressed from a recombinant expression vector in the recombinant microorganism.

3. The recombinant microorganism according to claim 1, wherein the recombinant microorganism is a microorganism comprising the ability to accumulate lactate.

4. The recombinant microorganism according to claim 3, wherein the microorganism comprising the ability to accumulate lactate is of the *Escherichia coli* strain Jw2293, Jw0885, or Jw0886.

5. A method for producing a polyester copolymer consisting of 3-hydroxybutyrate and lactate, which comprises the steps of:
(1) culturing a recombinant microorganism of claim 1 in a medium containing a carbon source to produce a polyester copolymer consisting of 3-hydroxybutyrate and lactate; and
(2) collecting the polyester copolymer consisting of 3-hydroxybutyrate and lactate from the culture in step (1).

6. The production method according to claim 5, wherein any one of said proteins is encoded by a polynucleotide expressed from a recombinant expression vector in the recombinant microorganism.

7. The production method according to claim 5, wherein culturing the recombinant microorganism is carried out under anaerobic conditions.

8. The production method according to claim 5, wherein the recombinant microorganism is a microorganism comprising the ability to accumulate lactate.

9. The production method according to claim 8, wherein the microorganism comprising the ability to accumulate lactate is of the *Escherichia coli* strain Jw2293, Jw0885, or Jw0886.

* * * * *

SEQUENCE LISTING

<160> NUMBER OF SEQ ID NOS: 8

<210> SEQ ID NO 1
<211> LENGTH: 1677
<212> TYPE: DNA
<213> ORGANISM: Pseudomonas sp.61-3
<220> FEATURE:
<221> NAME/KEY: CDS
<222> LOCATION: (1)..(1677)

<400> SEQUENCE: 1

```
atg agt aac aag aat agc gat gac ttg aat cgt caa gcc tcg gaa aac      48
Met Ser Asn Lys Asn Ser Asp Asp Leu Asn Arg Gln Ala Ser Glu Asn
1               5                  10                  15 acc ttg ggg ctt aac cct gtc atc ggc ctg cgt gga aaa gat ctg ctg      96
Thr Leu Gly Leu Asn Pro Val Ile Gly Leu Arg Gly Lys Asp Leu Leu
            20                  25                  30
```

| | |
|---|---:|
| act tct gcc cga atg gtt tta acc caa gcc atc aaa caa ccc att cac<br>Thr Ser Ala Arg Met Val Leu Thr Gln Ala Ile Lys Gln Pro Ile His<br>        35                    40                    45 | 144 |
| agc gtc aag cac gtc gcg cat ttt ggc atc gag ctg aag aac gtg atg<br>Ser Val Lys His Val Ala His Phe Gly Ile Glu Leu Lys Asn Val Met<br>  50                    55                    60 | 192 |
| ttt ggc aaa tcg aag ctg caa ccg gaa agc gat gac cgt cgt ttc aac<br>Phe Gly Lys Ser Lys Leu Gln Pro Glu Ser Asp Asp Arg Arg Phe Asn<br>65                    70                    75                    80 | 240 |
| gac ccc gcc tgg agt cag aac cca ctc tac aaa cgt tat cta caa acc<br>Asp Pro Ala Trp Ser Gln Asn Pro Leu Tyr Lys Arg Tyr Leu Gln Thr<br>                      85                    90                    95 | 288 |
| tac ctg gcg tgg cgc aag gaa ctc cac gac tgg atc ggc aac agc aaa<br>Tyr Leu Ala Trp Arg Lys Glu Leu His Asp Trp Ile Gly Asn Ser Lys<br>                100               105               110 | 336 |
| ctg tcc gaa cag gac atc aat cgc gct cac ttc gtg atc acc ctg atg<br>Leu Ser Glu Gln Asp Ile Asn Arg Ala His Phe Val Ile Thr Leu Met<br>          115               120               125 | 384 |
| acc gaa gcc atg gcc ccg acc aac agt gcg gcc aat ccg gcg gcg gtc<br>Thr Glu Ala Met Ala Pro Thr Asn Ser Ala Ala Asn Pro Ala Ala Val<br>130                   135               140 | 432 |
| aaa cgc ttc ttc gaa acc ggc ggt aaa agc ctg ctc gac ggc ctc aca<br>Lys Arg Phe Phe Glu Thr Gly Gly Lys Ser Leu Leu Asp Gly Leu Thr<br>145                   150               155               160 | 480 |
| cat ctg gcc aag gac ctg gta aac aac ggc ggc atg ccg agc cag gtg<br>His Leu Ala Lys Asp Leu Val Asn Asn Gly Gly Met Pro Ser Gln Val<br>                165               170               175 | 528 |
| gac atg ggc gct ttc gaa gtc ggc aag agt ctg ggg acg act gaa ggt<br>Asp Met Gly Ala Phe Glu Val Gly Lys Ser Leu Gly Thr Thr Glu Gly<br>          180               185               190 | 576 |
| gca gtg gtt ttc cgc aac gac gtc ctc gaa ttg atc cag tac cgg ccg<br>Ala Val Val Phe Arg Asn Asp Val Leu Glu Leu Ile Gln Tyr Arg Pro<br>               195               200               205 | 624 |
| acc acc gaa cag gtg cat gag cga ccg ctg ctg gtg gtc cca ccg cag<br>Thr Thr Glu Gln Val His Glu Arg Pro Leu Leu Val Val Pro Pro Gln<br>210                   215               220 | 672 |
| atc aac aag ttt tat gtg ttt gac ctg agc ccg gat aaa agc ctg gcg<br>Ile Asn Lys Phe Tyr Val Phe Asp Leu Ser Pro Asp Lys Ser Leu Ala<br>225                   230               235               240 | 720 |
| cgc ttc tgc ctg agc aac aac cag caa acc ttt atc gtc agc tgg cgc<br>Arg Phe Cys Leu Ser Asn Asn Gln Gln Thr Phe Ile Val Ser Trp Arg<br>                   245               250               255 | 768 |
| aac ccg acc aag gcc cag cgt gag tgg ggt ctg tcg act tac atc gat<br>Asn Pro Thr Lys Ala Gln Arg Glu Trp Gly Leu Ser Thr Tyr Ile Asp<br>          260               265               270 | 816 |
| gcg ctc aaa gaa gcc gtc gac gta gtt tcc gcc atc acc ggc agc aaa<br>Ala Leu Lys Glu Ala Val Asp Val Val Ser Ala Ile Thr Gly Ser Lys<br>               275               280               285 | 864 |
| gac atc aac atg ctc ggc gcc tgc tcc ggt ggc att acc tgc acc gcg<br>Asp Ile Asn Met Leu Gly Ala Cys Ser Gly Gly Ile Thr Cys Thr Ala<br>290                   295               300 | 912 |
| ctg ctg ggt cac tac gcc gct ctc ggc gag aag aag gtc aat gcc ctg<br>Leu Leu Gly His Tyr Ala Ala Leu Gly Glu Lys Lys Val Asn Ala Leu<br>305                   310               315               320 | 960 |
| acc ctt ttg gtc agc gtg ctc gac acc acc ctc gac tcc cag gtt gca<br>Thr Leu Leu Val Ser Val Leu Asp Thr Thr Leu Asp Ser Gln Val Ala<br>                   325               330               335 | 1008 |
| ctg ttc gtc gat gag aaa acc ctg gaa gct gcc aag cgt cac tcg tat<br>Leu Phe Val Asp Glu Lys Thr Leu Glu Ala Ala Lys Arg His Ser Tyr<br>               340               345               350 | 1056 |

```
cag gcc ggc gtg ctg gaa ggc cgc gac atg gcc aaa gtc ttc gcc tgg      1104
Gln Ala Gly Val Leu Glu Gly Arg Asp Met Ala Lys Val Phe Ala Trp
        355                 360                 365 atg cgc cct aac gac ctg atc tgg aac tac tgg gtc aac aac tac ctg      1152
Met Arg Pro Asn Asp Leu Ile Trp Asn Tyr Trp Val Asn Asn Tyr Leu
370                 375                 380 ctg ggt aac gag cca ccg gtc ttc gac att ctt ttc tgg aac aac gac      1200
Leu Gly Asn Glu Pro Pro Val Phe Asp Ile Leu Phe Trp Asn Asn Asp
385                 390                 395                 400 acc acc cgg ttg cct gct gcg ttc cac ggc gat ctg atc gaa atg ttc      1248
Thr Thr Arg Leu Pro Ala Ala Phe His Gly Asp Leu Ile Glu Met Phe
            405                 410                 415 aaa aat aac cca ctg gtg cgc gcc aat gca ctc gaa gtg agc ggc acg      1296
Lys Asn Asn Pro Leu Val Arg Ala Asn Ala Leu Glu Val Ser Gly Thr
                420                 425                 430 ccg atc gac ctc aaa cag gtc act gcc gac atc tac tcc ctg gcc ggc      1344
Pro Ile Asp Leu Lys Gln Val Thr Ala Asp Ile Tyr Ser Leu Ala Gly
            435                 440                 445 acc aac gat cac atc acg ccc tgg aag tct tgc tac aag tcg gcg caa      1392
Thr Asn Asp His Ile Thr Pro Trp Lys Ser Cys Tyr Lys Ser Ala Gln
450                 455                 460 ctg ttc ggt ggc aag gtc gaa ttc gtg ctg tcc agc agt ggg cat atc      1440
Leu Phe Gly Gly Lys Val Glu Phe Val Leu Ser Ser Ser Gly His Ile
465                 470                 475                 480 cag agc att ctg aac ccg ccg ggc aat ccg aaa tca cgt tac atg acc      1488
Gln Ser Ile Leu Asn Pro Pro Gly Asn Pro Lys Ser Arg Tyr Met Thr
            485                 490                 495 agc acc gac atg cca gcc acc gcc aac gag tgg caa gaa aac tca acc      1536
Ser Thr Asp Met Pro Ala Thr Ala Asn Glu Trp Gln Glu Asn Ser Thr
                500                 505                 510 aag cac acc gac tcc tgg tgg ctg cac tgg cag gcc tgg cag gcc gag      1584
Lys His Thr Asp Ser Trp Trp Leu His Trp Gln Ala Trp Gln Ala Glu
            515                 520                 525 cgc tcg ggc aaa ctg aaa aag tcc ccg acc agc ctg ggc aac aag gcc      1632
Arg Ser Gly Lys Leu Lys Lys Ser Pro Thr Ser Leu Gly Asn Lys Ala
530                 535                 540 tat ccg tca gga gaa gcc gcg ccg ggc acg tat gtg cat gaa cgt           1677
Tyr Pro Ser Gly Glu Ala Ala Pro Gly Thr Tyr Val His Glu Arg
545                 550                 555

<210> SEQ ID NO 2
<211> LENGTH: 559
<212> TYPE: PRT
<213> ORGANISM: Pseudomonas sp.61-3

<400> SEQUENCE: 2

Met Ser Asn Lys Asn Ser Asp Asp Leu Asn Arg Gln Ala Ser Glu Asn
1               5                   10                  15

Thr Leu Gly Leu Asn Pro Val Ile Gly Leu Arg Gly Lys Asp Leu Leu
            20                  25                  30

Thr Ser Ala Arg Met Val Leu Thr Gln Ala Ile Lys Gln Pro Ile His
        35                  40                  45

Ser Val Lys His Val Ala His Phe Gly Ile Glu Leu Lys Asn Val Met
    50                  55                  60

Phe Gly Lys Ser Lys Leu Gln Pro Glu Ser Asp Asp Arg Arg Phe Asn
65                  70                  75                  80

Asp Pro Ala Trp Ser Gln Asn Pro Leu Tyr Lys Arg Tyr Leu Gln Thr
                85                  90                  95

Tyr Leu Ala Trp Arg Lys Glu Leu His Asp Trp Ile Gly Asn Ser Lys
            100                 105                 110
```

```
Leu Ser Glu Gln Asp Ile Asn Arg Ala His Phe Val Ile Thr Leu Met
        115                 120                 125

Thr Glu Ala Met Ala Pro Thr Asn Ser Ala Ala Asn Pro Ala Ala Val
130                 135                 140

Lys Arg Phe Phe Glu Thr Gly Gly Lys Ser Leu Leu Asp Gly Leu Thr
145                 150                 155                 160

His Leu Ala Lys Asp Leu Val Asn Asn Gly Gly Met Pro Ser Gln Val
                165                 170                 175

Asp Met Gly Ala Phe Glu Val Gly Lys Ser Leu Gly Thr Thr Glu Gly
            180                 185                 190

Ala Val Val Phe Arg Asn Asp Val Leu Glu Leu Ile Gln Tyr Arg Pro
        195                 200                 205

Thr Thr Glu Gln Val His Glu Arg Pro Leu Leu Val Val Pro Pro Gln
    210                 215                 220

Ile Asn Lys Phe Tyr Val Phe Asp Leu Ser Pro Asp Lys Ser Leu Ala
225                 230                 235                 240

Arg Phe Cys Leu Ser Asn Asn Gln Gln Thr Phe Ile Val Ser Trp Arg
                245                 250                 255

Asn Pro Thr Lys Ala Gln Arg Glu Trp Gly Leu Ser Thr Tyr Ile Asp
            260                 265                 270

Ala Leu Lys Glu Ala Val Asp Val Val Ser Ala Ile Thr Gly Ser Lys
        275                 280                 285

Asp Ile Asn Met Leu Gly Ala Cys Ser Gly Gly Ile Thr Cys Thr Ala
    290                 295                 300

Leu Leu Gly His Tyr Ala Ala Leu Gly Glu Lys Lys Val Asn Ala Leu
305                 310                 315                 320

Thr Leu Leu Val Ser Val Leu Asp Thr Thr Leu Asp Ser Gln Val Ala
                325                 330                 335

Leu Phe Val Asp Glu Lys Thr Leu Glu Ala Ala Lys Arg His Ser Tyr
            340                 345                 350

Gln Ala Gly Val Leu Glu Gly Arg Asp Met Ala Lys Val Phe Ala Trp
        355                 360                 365

Met Arg Pro Asn Asp Leu Ile Trp Asn Tyr Trp Val Asn Asn Tyr Leu
    370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Met Phe
                405                 410                 415

Lys Asn Asn Pro Leu Val Arg Ala Asn Ala Leu Glu Val Ser Gly Thr
            420                 425                 430

Pro Ile Asp Leu Lys Gln Val Thr Ala Asp Ile Tyr Ser Leu Ala Gly
        435                 440                 445

Thr Asn Asp His Ile Thr Pro Trp Lys Ser Cys Tyr Lys Ser Ala Gln
    450                 455                 460

Leu Phe Gly Gly Lys Val Glu Phe Val Leu Ser Ser Ser Gly His Ile
465                 470                 475                 480

Gln Ser Ile Leu Asn Pro Pro Gly Asn Pro Lys Ser Arg Tyr Met Thr
                485                 490                 495

Ser Thr Asp Met Pro Ala Thr Ala Asn Glu Trp Gln Glu Asn Ser Thr
            500                 505                 510

Lys His Thr Asp Ser Trp Trp Leu His Trp Gln Ala Trp Gln Ala Glu
    515                 520                 525

Arg Ser Gly Lys Leu Lys Lys Ser Pro Thr Ser Leu Gly Asn Lys Ala
```

```
                530                 535                 540
Tyr Pro Ser Gly Glu Ala Ala Pro Gly Thr Tyr Val His Glu Arg
545                 550                 555

<210> SEQ ID NO 3
<211> LENGTH: 1554
<212> TYPE: DNA
<213> ORGANISM: Megasphaera elsdenii
<220> FEATURE:
<221> NAME/KEY: CDS
<222> LOCATION: (1)..(1554)

<400> SEQUENCE: 3 atg aga aaa gta gaa atc att aca gct gaa caa gca gct cag ctc gta        48
Met Arg Lys Val Glu Ile Ile Thr Ala Glu Gln Ala Ala Gln Leu Val
1               5                   10                  15 aaa gac aac gac acg att acg tct atc ggc ttt gtc agc agc gcc cat       96
Lys Asp Asn Asp Thr Ile Thr Ser Ile Gly Phe Val Ser Ser Ala His
            20                  25                  30 ccg gaa gca ctg acc aaa gct ttg gaa aaa cgg ttc ctg gac acg aac      144
Pro Glu Ala Leu Thr Lys Ala Leu Glu Lys Arg Phe Leu Asp Thr Asn
        35                  40                  45 acc ccg cag aac ttg acc tac atc tat gca ggc tct cag ggt aaa cgc      192
Thr Pro Gln Asn Leu Thr Tyr Ile Tyr Ala Gly Ser Gln Gly Lys Arg
    50                  55                  60 gat ggc cgt gcc gct gaa cat ctg gca cac aca ggc ctt ttg aaa cgc      240
Asp Gly Arg Ala Ala Glu His Leu Ala His Thr Gly Leu Leu Lys Arg
65                  70                  75                  80 gcc atc atc ggt cac tgg cag act gta ccg gct atc ggt aaa ctg gct      288
Ala Ile Ile Gly His Trp Gln Thr Val Pro Ala Ile Gly Lys Leu Ala
                85                  90                  95 gtc gaa aac aag att gaa gct tac aac ttc tcg cag ggc acg ttg gtc      336
Val Glu Asn Lys Ile Glu Ala Tyr Asn Phe Ser Gln Gly Thr Leu Val
            100                 105                 110 cac tgg ttc cgc gcc ttg gca ggt cat aag ctc ggc gtc ttc acc gac      384
His Trp Phe Arg Ala Leu Ala Gly His Lys Leu Gly Val Phe Thr Asp
        115                 120                 125 atc ggt ctg gaa act ttc ctc gat ccc cgt cag ctc ggc ggc aag ctc      432
Ile Gly Leu Glu Thr Phe Leu Asp Pro Arg Gln Leu Gly Gly Lys Leu
    130                 135                 140 aat gac gta acc aaa gaa gac ctc gtc aaa ctg atc gaa gtc gat ggt      480
Asn Asp Val Thr Lys Glu Asp Leu Val Lys Leu Ile Glu Val Asp Gly
145                 150                 155                 160 cat gaa cag ctt ttc tac ccg acc ttc ccg gtc aac gta gct ttc ctc      528
His Glu Gln Leu Phe Tyr Pro Thr Phe Pro Val Asn Val Ala Phe Leu
                165                 170                 175 cgc ggt acg tat gct gat gaa tcc ggc aat atc acc atg gac gaa gaa      576
Arg Gly Thr Tyr Ala Asp Glu Ser Gly Asn Ile Thr Met Asp Glu Glu
            180                 185                 190 atc ggg cct ttc gaa agc act tcc gta gcc cag gcc gtt cac aac tgt      624
Ile Gly Pro Phe Glu Ser Thr Ser Val Ala Gln Ala Val His Asn Cys
        195                 200                 205 ggc ggt aaa gtc gtc gtc cag gtc aaa gac gtc gtc gct cac ggc agc      672
Gly Gly Lys Val Val Val Gln Val Lys Asp Val Val Ala His Gly Ser
    210                 215                 220 ctg gat ccg cgc atg gtc aaa atc cct ggc atc tat gtc gac tat gtt      720
Leu Asp Pro Arg Met Val Lys Ile Pro Gly Ile Tyr Val Asp Tyr Val
225                 230                 235                 240 gtc gta gct gct ccg gaa gac cat cag cag act tat gac tgc gaa tat      768
Val Val Ala Ala Pro Glu Asp His Gln Gln Thr Tyr Asp Cys Glu Tyr
                245                 250                 255
```

| | | |
|---|---|---|
| gat ccg tcc ctt agc ggc gaa cat cgt gct cct gaa ggc gct gct gac<br>Asp Pro Ser Leu Ser Gly Glu His Arg Ala Pro Glu Gly Ala Ala Asp<br>260                          265                          270 | 816 |
| gca gct ctc ccc atg agc gct aag aaa atc atc ggc cgc cgc ggt gct<br>Ala Ala Leu Pro Met Ser Ala Lys Lys Ile Ile Gly Arg Arg Gly Ala<br>275                          280                          285 | 864 |
| ttg gaa ttg acc gaa aac gct gtc gtc aac ctc ggc gtc ggc gct ccg<br>Leu Glu Leu Thr Glu Asn Ala Val Val Asn Leu Gly Val Gly Ala Pro<br>290                          295                          300 | 912 |
| gaa tac gtt gct tcc gtt gcc ggt gaa gaa ggt atc gct gat acc att<br>Glu Tyr Val Ala Ser Val Ala Gly Glu Glu Gly Ile Ala Asp Thr Ile<br>305                          310                          315                    320 | 960 |
| acc ttg acc gtc gaa ggt ggc gct atc ggt ggt gta ccg cag ggc ggt<br>Thr Leu Thr Val Glu Gly Gly Ala Ile Gly Gly Val Pro Gln Gly Gly<br>                        325                          330                          335 | 1008 |
| gcc cgc ttc ggt tcg tcc cgt aat gct gat gcc atc atc gac cat act<br>Ala Arg Phe Gly Ser Ser Arg Asn Ala Asp Ala Ile Ile Asp His Thr<br>                        340                          345                          350 | 1056 |
| tac cag ttc gac ttc tat gat ggc ggc ggt ctg gac atc gct tac ctc<br>Tyr Gln Phe Asp Phe Tyr Asp Gly Gly Gly Leu Asp Ile Ala Tyr Leu<br>                  355                          360                          365 | 1104 |
| ggc ctg gct cag tgc gat ggt tcg ggc aac atc aac gtc agc aag ttc<br>Gly Leu Ala Gln Cys Asp Gly Ser Gly Asn Ile Asn Val Ser Lys Phe<br>370                          375                          380 | 1152 |
| ggt act aac gtt gcc ggc tgt ggc ggt ttc ccc aac att tcc cag cag<br>Gly Thr Asn Val Ala Gly Cys Gly Gly Phe Pro Asn Ile Ser Gln Gln<br>385                          390                          395                    400 | 1200 |
| aca ccg aat gtt tac ttc tgc ggc acc ttc acg gct ggc ggc ttg aaa<br>Thr Pro Asn Val Tyr Phe Cys Gly Thr Phe Thr Ala Gly Gly Leu Lys<br>                        405                          410                          415 | 1248 |
| atc gct gtc gaa gac ggc aaa gtc aag atc ctc cag gaa ggc aaa gcc<br>Ile Ala Val Glu Asp Gly Lys Val Lys Ile Leu Gln Glu Gly Lys Ala<br>                  420                          425                          430 | 1296 |
| aag aag ttc atc aaa gct gtc gac cag atc act ttc aac ggt tct tat<br>Lys Lys Phe Ile Lys Ala Val Asp Gln Ile Thr Phe Asn Gly Ser Tyr<br>                435                          440                          445 | 1344 |
| gca gcc cgc aac ggc aaa cat gtt ctc tac atc acg gaa cgc tgc gta<br>Ala Ala Arg Asn Gly Lys His Val Leu Tyr Ile Thr Glu Arg Cys Val<br>450                          455                          460 | 1392 |
| ttt gaa ctg acc aaa gaa ggc ttg aaa ctc atc gaa gtc gca ccg ggc<br>Phe Glu Leu Thr Lys Glu Gly Leu Lys Leu Ile Glu Val Ala Pro Gly<br>465                          470                          475                    480 | 1440 |
| atc gat att gaa aaa gat atc ctc gct cac atg gac ttc aag ccg atc<br>Ile Asp Ile Glu Lys Asp Ile Leu Ala His Met Asp Phe Lys Pro Ile<br>                  485                          490                          495 | 1488 |
| att gat aat ccg aaa ctc atg gat gcc cgc ctc ttc cag gac ggt ccc<br>Ile Asp Asn Pro Lys Leu Met Asp Ala Arg Leu Phe Gln Asp Gly Pro<br>                500                          505                          510 | 1536 |
| atg gga ctg aaa aaa taa<br>Met Gly Leu Lys Lys<br>              515 | 1554 |

<210> SEQ ID NO 4
<211> LENGTH: 517
<212> TYPE: PRT
<213> ORGANISM: Megasphaera elsdenii

<400> SEQUENCE: 4

Met Arg Lys Val Glu Ile Ile Thr Ala Glu Gln Ala Ala Gln Leu Val
1                  5                      10                      15

Lys Asp Asn Asp Thr Ile Thr Ser Ile Gly Phe Val Ser Ser Ala His

-continued

```
                20                  25                  30
Pro Glu Ala Leu Thr Lys Ala Leu Glu Lys Arg Phe Leu Asp Thr Asn
             35                  40                  45
Thr Pro Gln Asn Leu Thr Tyr Ile Tyr Ala Gly Ser Gln Gly Lys Arg
 50                  55                  60
Asp Gly Arg Ala Ala Glu His Leu Ala His Thr Gly Leu Leu Lys Arg
 65                  70                  75                  80
Ala Ile Ile Gly His Trp Gln Thr Val Pro Ala Ile Gly Lys Leu Ala
                 85                  90                  95
Val Glu Asn Lys Ile Glu Ala Tyr Asn Phe Ser Gln Gly Thr Leu Val
                100                 105                 110
His Trp Phe Arg Ala Leu Ala Gly His Lys Leu Gly Val Phe Thr Asp
            115                 120                 125
Ile Gly Leu Glu Thr Phe Leu Asp Pro Arg Gln Leu Gly Gly Lys Leu
        130                 135                 140
Asn Asp Val Thr Lys Glu Asp Leu Val Lys Leu Ile Glu Val Asp Gly
145                 150                 155                 160
His Glu Gln Leu Phe Tyr Pro Thr Phe Pro Val Asn Val Ala Phe Leu
                165                 170                 175
Arg Gly Thr Tyr Ala Asp Glu Ser Gly Asn Ile Thr Met Asp Glu Glu
            180                 185                 190
Ile Gly Pro Phe Glu Ser Thr Ser Val Ala Gln Ala Val His Asn Cys
        195                 200                 205
Gly Gly Lys Val Val Gln Val Lys Asp Val Ala His Gly Ser
210                 215                 220
Leu Asp Pro Arg Met Val Lys Ile Pro Gly Ile Tyr Val Asp Tyr Val
225                 230                 235                 240
Val Val Ala Ala Pro Glu Asp His Gln Gln Thr Tyr Asp Cys Glu Tyr
                245                 250                 255
Asp Pro Ser Leu Ser Gly Glu His Arg Ala Pro Glu Gly Ala Ala Asp
            260                 265                 270
Ala Ala Leu Pro Met Ser Ala Lys Lys Ile Ile Gly Arg Arg Gly Ala
        275                 280                 285
Leu Glu Leu Thr Glu Asn Ala Val Asn Leu Gly Val Gly Ala Pro
290                 295                 300
Glu Tyr Val Ala Ser Val Ala Gly Glu Glu Ile Ala Asp Thr Ile
305                 310                 315                 320
Thr Leu Thr Val Glu Gly Gly Ala Ile Gly Gly Val Pro Gln Gly Gly
                325                 330                 335
Ala Arg Phe Gly Ser Ser Arg Asn Ala Asp Ala Ile Ile Asp His Thr
            340                 345                 350
Tyr Gln Phe Asp Phe Tyr Asp Gly Gly Leu Asp Ile Ala Tyr Leu
        355                 360                 365
Gly Leu Ala Gln Cys Asp Gly Ser Gly Asn Ile Asn Val Ser Lys Phe
    370                 375                 380
Gly Thr Asn Val Ala Gly Cys Gly Gly Phe Pro Asn Ile Ser Gln Gln
385                 390                 395                 400
Thr Pro Asn Val Tyr Phe Cys Gly Thr Phe Thr Ala Gly Gly Leu Lys
                405                 410                 415
Ile Ala Val Glu Asp Gly Lys Val Lys Ile Leu Gln Glu Gly Lys Ala
            420                 425                 430
Lys Lys Phe Ile Lys Ala Val Asp Gln Ile Thr Phe Asn Gly Ser Tyr
        435                 440                 445
```

```
Ala Ala Arg Asn Gly Lys His Val Leu Tyr Ile Thr Glu Arg Cys Val
        450                 455                 460

Phe Glu Leu Thr Lys Glu Gly Leu Lys Leu Ile Glu Val Ala Pro Gly
465                 470                 475                 480

Ile Asp Ile Glu Lys Asp Ile Leu Ala His Met Asp Phe Lys Pro Ile
                485                 490                 495

Ile Asp Asn Pro Lys Leu Met Asp Ala Arg Leu Phe Gln Asp Gly Pro
                500                 505                 510

Met Gly Leu Lys Lys
        515

<210> SEQ ID NO 5
<211> LENGTH: 1179
<212> TYPE: DNA
<213> ORGANISM: Ralstonia eutropha
<220> FEATURE:
<221> NAME/KEY: CDS
<222> LOCATION: (1)..(1179)

<400> SEQUENCE: 5 atg act gac gtt gtc atc gta tcc gcc gcc cgc acc gcg gtc ggc aag      48
Met Thr Asp Val Val Ile Val Ser Ala Ala Arg Thr Ala Val Gly Lys
1               5                   10                  15 ttt ggc ggc tcg ctg gcc aag atc ccg gca ccg gaa ctg ggt gcc gtg      96
Phe Gly Gly Ser Leu Ala Lys Ile Pro Ala Pro Glu Leu Gly Ala Val
            20                  25                  30 gtc atc aag gcc gcg ctg gag cgc gcc ggc gtc aag ccg gag cag gtg     144
Val Ile Lys Ala Ala Leu Glu Arg Ala Gly Val Lys Pro Glu Gln Val
        35                  40                  45 agc gaa gtc atc atg ggc cag gtg ctg acc gcc ggt tcg ggc cag aac     192
Ser Glu Val Ile Met Gly Gln Val Leu Thr Ala Gly Ser Gly Gln Asn
    50                  55                  60 ccc gca cgc cag gcc gcg atc aag gcc ggc ctg ccg gcg atg gtg ccg     240
Pro Ala Arg Gln Ala Ala Ile Lys Ala Gly Leu Pro Ala Met Val Pro
65                  70                  75                  80 gcc atg acc atc aac aag gtg tgc ggc tcg ggc ctg aag gcc gtg atg     288
Ala Met Thr Ile Asn Lys Val Cys Gly Ser Gly Leu Lys Ala Val Met
                85                  90                  95 ctg gcc gcc aac gcg atc atg gcg ggc gac gcc gag atc gtg gtg gcc     336
Leu Ala Ala Asn Ala Ile Met Ala Gly Asp Ala Glu Ile Val Val Ala
            100                 105                 110 ggc ggc cag gaa aac atg agc gcc gcc ccg cac gtg ctg ccg ggc tcg     384
Gly Gly Gln Glu Asn Met Ser Ala Ala Pro His Val Leu Pro Gly Ser
        115                 120                 125 cgc gat ggt ttc cgc atg ggc gat gcc aag ctg gtc gac acc atg atc     432
Arg Asp Gly Phe Arg Met Gly Asp Ala Lys Leu Val Asp Thr Met Ile
    130                 135                 140 gtc gac ggc ctg tgg gac gtg tac aac cag tac cac atg ggc atc acc     480
Val Asp Gly Leu Trp Asp Val Tyr Asn Gln Tyr His Met Gly Ile Thr
145                 150                 155                 160 gcc gag aac gtg gcc aag gaa tac ggc atc aca cgc gag gcg cag gat     528
Ala Glu Asn Val Ala Lys Glu Tyr Gly Ile Thr Arg Glu Ala Gln Asp
                165                 170                 175 gag ttc gcc gtc ggc tcg cag aac aag gcc gaa gcc gcg cag aag gcc     576
Glu Phe Ala Val Gly Ser Gln Asn Lys Ala Glu Ala Ala Gln Lys Ala
            180                 185                 190 ggc aag ttt gac gaa gag atc gtc ccg gtg ctg atc ccg cag cgc aag     624
Gly Lys Phe Asp Glu Glu Ile Val Pro Val Leu Ile Pro Gln Arg Lys
        195                 200                 205 ggc gac ccg gtg gcc ttc aag acc gac gag ttc gtg cgc cag ggc gcc     672
Gly Asp Pro Val Ala Phe Lys Thr Asp Glu Phe Val Arg Gln Gly Ala
```

```
                         210                 215                 220
acg ctg gac agc atg tcc ggc ctc aag ccc gcc ttc gac aag gcc ggc       720
Thr Leu Asp Ser Met Ser Gly Leu Lys Pro Ala Phe Asp Lys Ala Gly
225                 230                 235                 240 acg gtg acc gcg gcc aac gcc tcg ggc ctg aac gac ggc gcc gcc gcg       768
Thr Val Thr Ala Ala Asn Ala Ser Gly Leu Asn Asp Gly Ala Ala Ala
                245                 250                 255 gtg gtg gtg atg tcg gcg gcc aag gcc aag gaa ctg ggc ctg acc ccg       816
Val Val Val Met Ser Ala Ala Lys Ala Lys Glu Leu Gly Leu Thr Pro
            260                 265                 270 ctg gcc acg atc aag agc tat gcc aac gcc ggt gtc gat ccc aag gtg       864
Leu Ala Thr Ile Lys Ser Tyr Ala Asn Ala Gly Val Asp Pro Lys Val
        275                 280                 285 atg ggc atg ggc ccg gtg ccg gcc tcc aag cgc gcc ctg tcg cgc gcc       912
Met Gly Met Gly Pro Val Pro Ala Ser Lys Arg Ala Leu Ser Arg Ala
    290                 295                 300 gag tgg acc ccg caa gac ctg gac ctg atg gag atc aac gag gcc ttt       960
Glu Trp Thr Pro Gln Asp Leu Asp Leu Met Glu Ile Asn Glu Ala Phe
305                 310                 315                 320 gcc gcg cag gcg ctg gcg gtg cac cag cag atg ggc tgg gac acc tcc      1008
Ala Ala Gln Ala Leu Ala Val His Gln Gln Met Gly Trp Asp Thr Ser
                325                 330                 335 aag gtc aat gtg aac ggc ggc gcc atc gcc atc ggc cac ccg atc ggc      1056
Lys Val Asn Val Asn Gly Gly Ala Ile Ala Ile Gly His Pro Ile Gly
            340                 345                 350 gcg tcg ggc tgc cgt atc ctg gtg acg ctg ctg cac gag atg aag cgc      1104
Ala Ser Gly Cys Arg Ile Leu Val Thr Leu Leu His Glu Met Lys Arg
        355                 360                 365 cgt gac gcg aag aag ggc ctg gcc tcg ctg tgc atc ggc ggc ggc atg      1152
Arg Asp Ala Lys Lys Gly Leu Ala Ser Leu Cys Ile Gly Gly Gly Met
    370                 375                 380 ggc gtg gcg ctg gca gtc gag cgc aaa                                  1179
Gly Val Ala Leu Ala Val Glu Arg Lys
385                 390
```

<210> SEQ ID NO 6
<211> LENGTH: 393
<212> TYPE: PRT
<213> ORGANISM: Ralstonia eutropha

<400> SEQUENCE: 6

```
Met Thr Asp Val Val Ile Val Ser Ala Ala Arg Thr Ala Val Gly Lys
1               5                   10                  15

Phe Gly Gly Ser Leu Ala Lys Ile Pro Ala Pro Glu Leu Gly Ala Val
                20                  25                  30

Val Ile Lys Ala Ala Leu Glu Arg Ala Gly Val Lys Pro Glu Gln Val
            35                  40                  45

Ser Glu Val Ile Met Gly Gln Val Leu Thr Ala Gly Ser Gly Gln Asn
        50                  55                  60

Pro Ala Arg Gln Ala Ala Ile Lys Ala Gly Leu Pro Ala Met Val Pro
65                  70                  75                  80

Ala Met Thr Ile Asn Lys Val Cys Gly Ser Gly Leu Lys Ala Val Met
                85                  90                  95

Leu Ala Ala Asn Ala Ile Met Ala Gly Asp Ala Glu Ile Val Val Ala
            100                 105                 110

Gly Gly Gln Glu Asn Met Ser Ala Ala Pro His Val Leu Pro Gly Ser
        115                 120                 125

Arg Asp Gly Phe Arg Met Gly Asp Ala Lys Leu Val Asp Thr Met Ile
    130                 135                 140
```

```
Val Asp Gly Leu Trp Asp Val Tyr Asn Gln Tyr His Met Gly Ile Thr
145                 150                 155                 160

Ala Glu Asn Val Ala Lys Glu Tyr Gly Ile Thr Arg Glu Ala Gln Asp
            165                 170                 175

Glu Phe Ala Val Gly Ser Gln Asn Lys Ala Glu Ala Ala Gln Lys Ala
        180                 185                 190

Gly Lys Phe Asp Glu Ile Val Pro Val Leu Ile Pro Gln Arg Lys
    195                 200                 205

Gly Asp Pro Val Ala Phe Lys Thr Asp Glu Phe Val Arg Gln Gly Ala
    210                 215                 220

Thr Leu Asp Ser Met Ser Gly Leu Lys Pro Ala Phe Asp Lys Ala Gly
225                 230                 235                 240

Thr Val Thr Ala Ala Asn Ala Ser Gly Leu Asn Asp Gly Ala Ala Ala
                245                 250                 255

Val Val Val Met Ser Ala Ala Lys Ala Lys Glu Leu Gly Leu Thr Pro
            260                 265                 270

Leu Ala Thr Ile Lys Ser Tyr Ala Asn Ala Gly Val Asp Pro Lys Val
        275                 280                 285

Met Gly Met Gly Pro Val Pro Ala Ser Lys Arg Ala Leu Ser Arg Ala
    290                 295                 300

Glu Trp Thr Pro Gln Asp Leu Asp Leu Met Glu Ile Asn Glu Ala Phe
305                 310                 315                 320

Ala Ala Gln Ala Leu Ala Val His Gln Gln Met Gly Trp Asp Thr Ser
                325                 330                 335

Lys Val Asn Val Asn Gly Gly Ala Ile Ala Ile Gly His Pro Ile Gly
            340                 345                 350

Ala Ser Gly Cys Arg Ile Leu Val Thr Leu Leu His Glu Met Lys Arg
        355                 360                 365

Arg Asp Ala Lys Lys Gly Leu Ala Ser Leu Cys Ile Gly Gly Gly Met
    370                 375                 380

Gly Val Ala Leu Ala Val Glu Arg Lys
385                 390

<210> SEQ ID NO 7
<211> LENGTH: 738
<212> TYPE: DNA
<213> ORGANISM: Ralstonia eutropha
<220> FEATURE:
<221> NAME/KEY: CDS
<222> LOCATION: (1)..(738)

<400> SEQUENCE: 7 atg act cag cgc att gcg tat gtg acc ggc ggc atg ggt ggt atc gga    48
Met Thr Gln Arg Ile Ala Tyr Val Thr Gly Gly Met Gly Gly Ile Gly
1               5                   10                  15 acc gcc att tgc cag cgg ctg gcc aag gat ggc ttt cgt gtg gtg gcc    96
Thr Ala Ile Cys Gln Arg Leu Ala Lys Asp Gly Phe Arg Val Val Ala
            20                  25                  30 ggt tgc ggc ccc aac tcg ccg cgc cgc gaa aag tgg ctg gag cag cag   144
Gly Cys Gly Pro Asn Ser Pro Arg Arg Glu Lys Trp Leu Glu Gln Gln
        35                  40                  45 aag gcc ctg ggc ttc gat ttc att gcc tcg gaa ggc aat gtg gct gac   192
Lys Ala Leu Gly Phe Asp Phe Ile Ala Ser Glu Gly Asn Val Ala Asp
    50                  55                  60 tgg gac tcg acc aag acc gca ttc gac aag gtc aag tcc gag gtc ggc   240
Trp Asp Ser Thr Lys Thr Ala Phe Asp Lys Val Lys Ser Glu Val Gly
65                  70                  75                  80
```

```
gag gtt gat gtg ctg atc aac aac gcc ggt atc acc cgc gac gtg gtg       288
Glu Val Asp Val Leu Ile Asn Asn Ala Gly Ile Thr Arg Asp Val Val
             85                  90                  95 ttc cgc aag atg acc cgc gcc gac tgg gat gcg gtg atc gac acc aac       336
Phe Arg Lys Met Thr Arg Ala Asp Trp Asp Ala Val Ile Asp Thr Asn
            100                 105                 110 ctg acc tcg ctg ttc aac gtc acc aag cag gtg atc gac ggc atg gcc       384
Leu Thr Ser Leu Phe Asn Val Thr Lys Gln Val Ile Asp Gly Met Ala
        115                 120                 125 gac cgt ggc tgg ggc cgc atc gtc aac atc tcg tcg gtg aac ggg cag       432
Asp Arg Gly Trp Gly Arg Ile Val Asn Ile Ser Ser Val Asn Gly Gln
    130                 135                 140 aag ggc cag ttc ggc cag acc aac tac tcc acc gcc aag gcc ggc ctg       480
Lys Gly Gln Phe Gly Gln Thr Asn Tyr Ser Thr Ala Lys Ala Gly Leu
145                 150                 155                 160 cat ggc ttc acc atg gca ctg gcg cag gaa gtg gcg acc aag ggc gtg       528
His Gly Phe Thr Met Ala Leu Ala Gln Glu Val Ala Thr Lys Gly Val
                165                 170                 175 acc gtc aac acg gtc tct ccg ggc tat atc gcc acc gac atg gtc aag       576
Thr Val Asn Thr Val Ser Pro Gly Tyr Ile Ala Thr Asp Met Val Lys
            180                 185                 190 gcg atc cgc cag gac gtg ctc gac aag atc gtc gcg acg atc ccg gtc       624
Ala Ile Arg Gln Asp Val Leu Asp Lys Ile Val Ala Thr Ile Pro Val
        195                 200                 205 aag cgc ctg ggc ctg ccg gaa gag atc gcc tcg atc tgc gcc tgg ttg       672
Lys Arg Leu Gly Leu Pro Glu Glu Ile Ala Ser Ile Cys Ala Trp Leu
    210                 215                 220 tcg tcg gag gag tcc ggt ttc tcg acc ggc gcc gac ttc tcg ctc aac       720
Ser Ser Glu Glu Ser Gly Phe Ser Thr Gly Ala Asp Phe Ser Leu Asn
225                 230                 235                 240 ggc ggc ctg cat atg ggc                                               738
Gly Gly Leu His Met Gly
                245

<210> SEQ ID NO 8
<211> LENGTH: 246
<212> TYPE: PRT
<213> ORGANISM: Ralstonia eutropha

<400> SEQUENCE: 8

Met Thr Gln Arg Ile Ala Tyr Val Thr Gly Gly Met Gly Gly Ile Gly
1               5                   10                  15

Thr Ala Ile Cys Gln Arg Leu Ala Lys Asp Gly Phe Arg Val Val Ala
            20                  25                  30

Gly Cys Gly Pro Asn Ser Pro Arg Arg Glu Lys Trp Leu Glu Gln Gln
        35                  40                  45

Lys Ala Leu Gly Phe Asp Phe Ile Ala Ser Glu Gly Asn Val Ala Asp
    50                  55                  60

Trp Asp Ser Thr Lys Thr Ala Phe Asp Lys Val Lys Ser Glu Val Gly
65                  70                  75                  80

Glu Val Asp Val Leu Ile Asn Asn Ala Gly Ile Thr Arg Asp Val Val
                85                  90                  95

Phe Arg Lys Met Thr Arg Ala Asp Trp Asp Ala Val Ile Asp Thr Asn
            100                 105                 110

Leu Thr Ser Leu Phe Asn Val Thr Lys Gln Val Ile Asp Gly Met Ala
        115                 120                 125

Asp Arg Gly Trp Gly Arg Ile Val Asn Ile Ser Ser Val Asn Gly Gln
    130                 135                 140

Lys Gly Gln Phe Gly Gln Thr Asn Tyr Ser Thr Ala Lys Ala Gly Leu
```

-continued

```
            145                 150                 155                 160
His Gly Phe Thr Met Ala Leu Ala Gln Glu Val Ala Thr Lys Gly Val
                    165                 170                 175

Thr Val Asn Thr Val Ser Pro Gly Tyr Ile Ala Thr Asp Met Val Lys
            180                 185                 190

Ala Ile Arg Gln Asp Val Leu Asp Lys Ile Val Ala Thr Ile Pro Val
        195                 200                 205

Lys Arg Leu Gly Leu Pro Glu Glu Ile Ala Ser Ile Cys Ala Trp Leu
    210                 215                 220

Ser Ser Glu Glu Ser Gly Phe Ser Thr Gly Ala Asp Phe Ser Leu Asn
225                 230                 235                 240

Gly Gly Leu His Met Gly
                245
```